United States Patent
Nakano et al.

(10) Patent No.: US 10,258,366 B2
(45) Date of Patent: Apr. 16, 2019

(54) MEDICAL DEVICE

(71) Applicant: TERUMO KABUSHIKI KAISHA, Shibuya-ku, Tokyo (JP)

(72) Inventors: Taiga Nakano, Sunnyvale, CA (US); Junichi Kobayashi, Cupertino, CA (US); Tomonori Hatta, Cupertino, CA (US)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 167 days.

(21) Appl. No.: 15/171,839

(22) Filed: Jun. 2, 2016

(65) Prior Publication Data

US 2016/0354108 A1 Dec. 8, 2016

(30) Foreign Application Priority Data

Jun. 2, 2015 (JP) ................................ 2015-112096

(51) Int. Cl.
| | |
|---|---|
| *A61B 17/3207* | (2006.01) |
| *A61B 17/221* | (2006.01) |
| *A61B 17/00* | (2006.01) |
| *A61B 17/22* | (2006.01) |
| *A61B 90/00* | (2016.01) |

(52) U.S. Cl.
CPC .... *A61B 17/320758* (2013.01); *A61B 17/221* (2013.01); *A61B 17/320725* (2013.01); *A61B 2017/00017* (2013.01); *A61B 2017/00398* (2013.01); *A61B 2017/00867* (2013.01); *A61B 2017/2212* (2013.01); *A61B 2017/22079* (2013.01); *A61B 2090/064* (2016.02)

(58) Field of Classification Search
CPC ........ A61B 17/3207; A61B 17/320725; A61B 17/320758; A61B 17/221; A61B 2017/2212; A61B 2017/00398
See application file for complete search history.

(56) References Cited

U.S. PATENT DOCUMENTS

| | | | | |
|---|---|---|---|---|
| 5,836,868 A | * | 11/1998 | Ressemann | 606/159 |
| 6,077,165 A | * | 6/2000 | Jewell | F16D 3/52 |
| | | | | 464/88 |
| 2001/0031981 A1 | * | 10/2001 | Evans | A61B 17/221 |
| | | | | 606/200 |
| 2004/0158270 A1 | | 8/2004 | Wyzgala et al. | |

FOREIGN PATENT DOCUMENTS

| | | |
|---|---|---|
| JP | 2003-504090 A | 2/2003 |
| WO | WO 99/044513 A2 | 9/1999 |

* cited by examiner

*Primary Examiner* — Thomas M McEvoy
(74) *Attorney, Agent, or Firm* — Buchanan Ingersoll & Rooney PC

(57) ABSTRACT

A medical device for incising a substance inside a biological lumen. The medical device includes a tubular drive shaft that is rotatable, an intermediate portion connected to the drive shaft, at least one strut interlocked with the drive shaft, a tubular linear motion shaft inside of the drive shaft, and a tubular interlock portion. The strut is rotatable with the drive shaft and is expandable radially outward in response to outward expansion of the intermediate portion. The linear motion shaft is movable relative to the drive shaft in the axial direction to cause the strut to expand radially outward. The tubular interlock portion interlocks the drive shaft and the linear motion shaft while maintaining liquid-tight properties. The tubular interlock portion is stretchable in the axial direction.

6 Claims, 28 Drawing Sheets

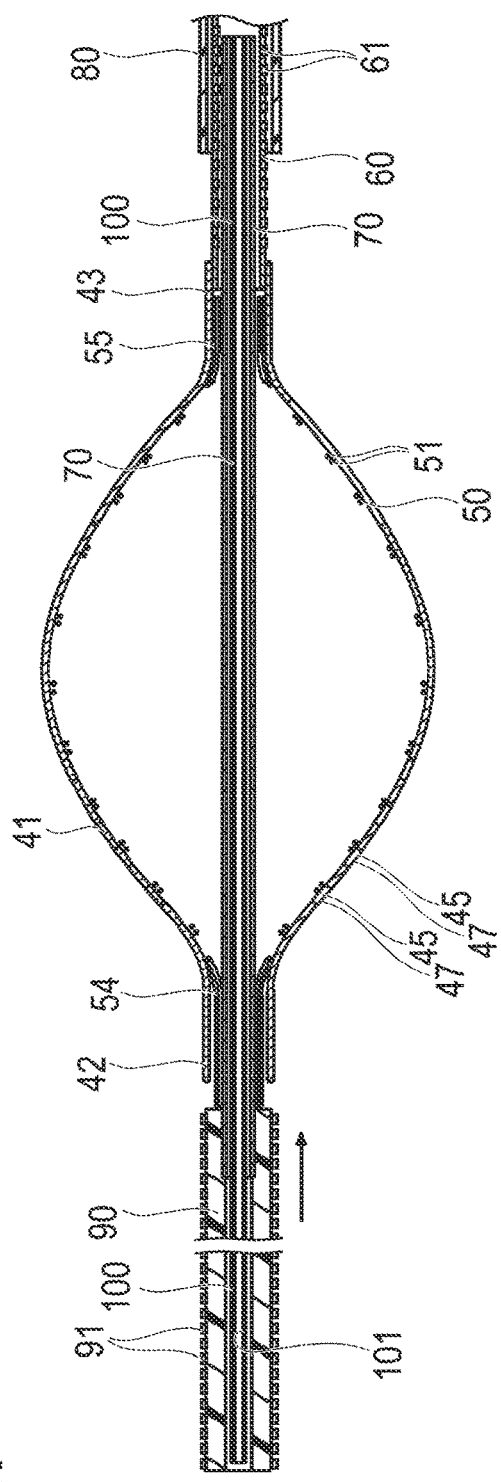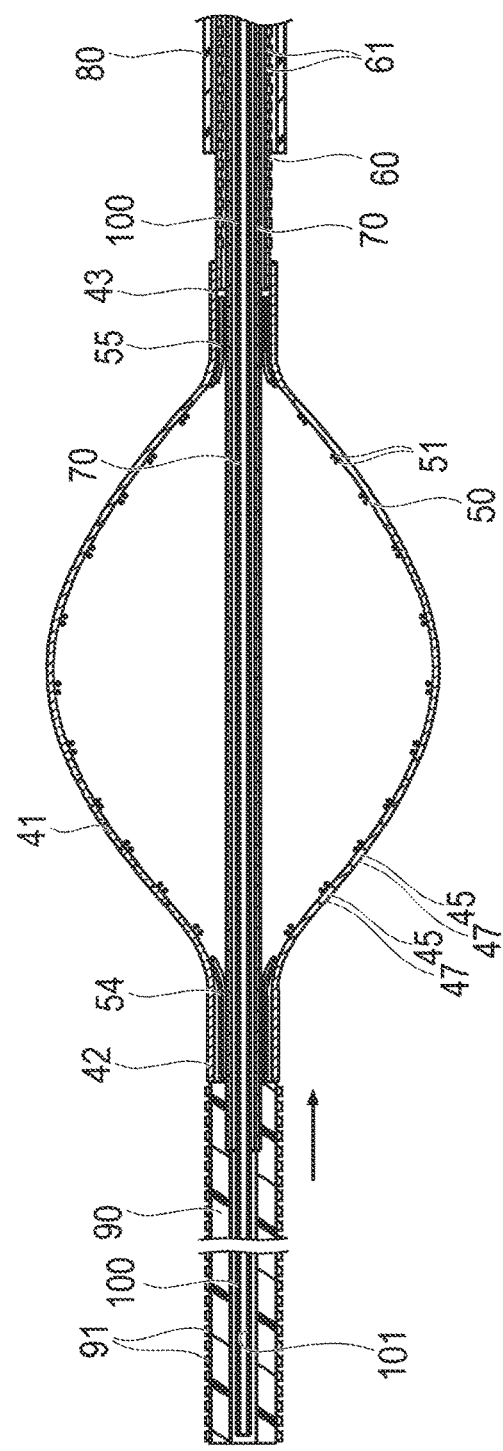

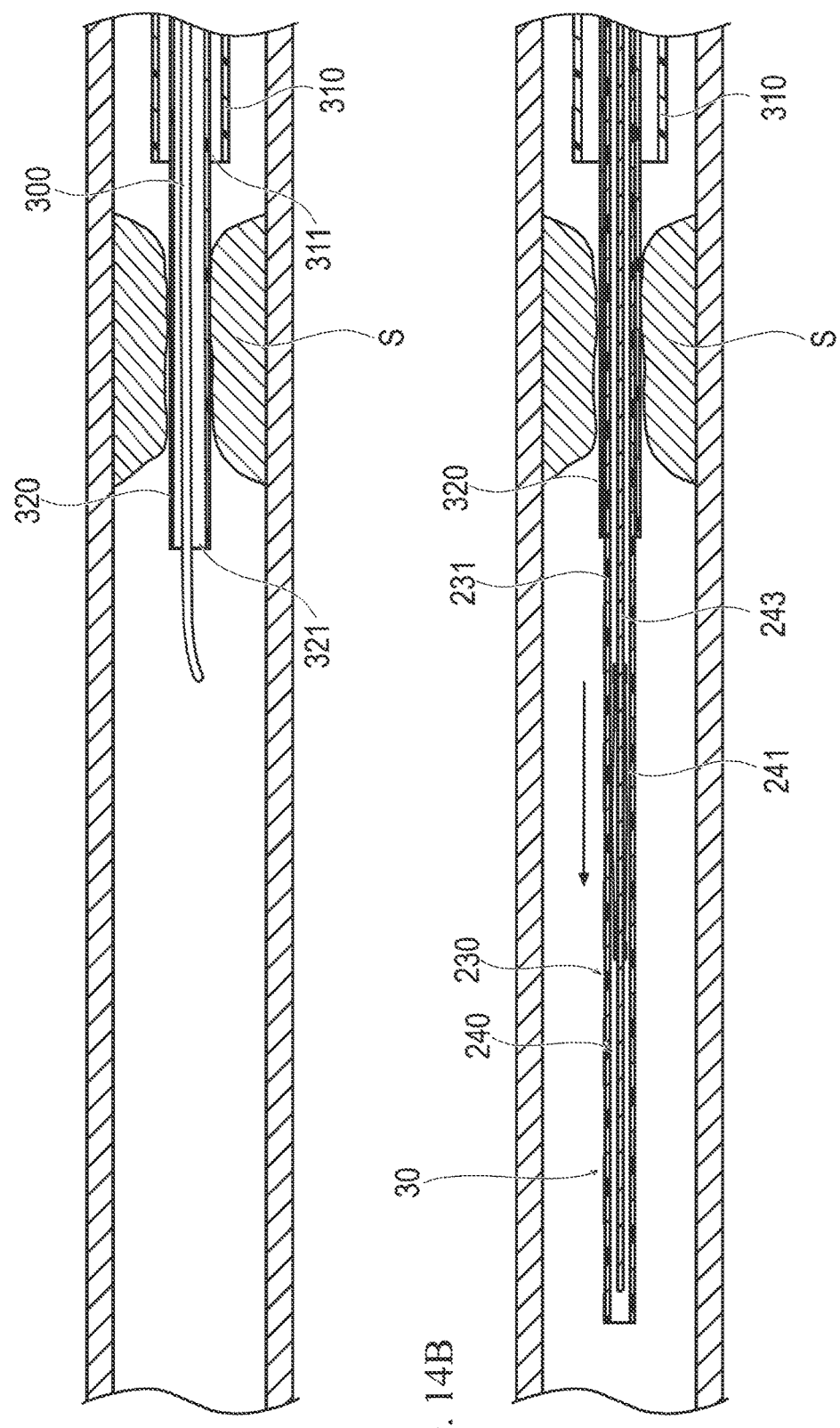

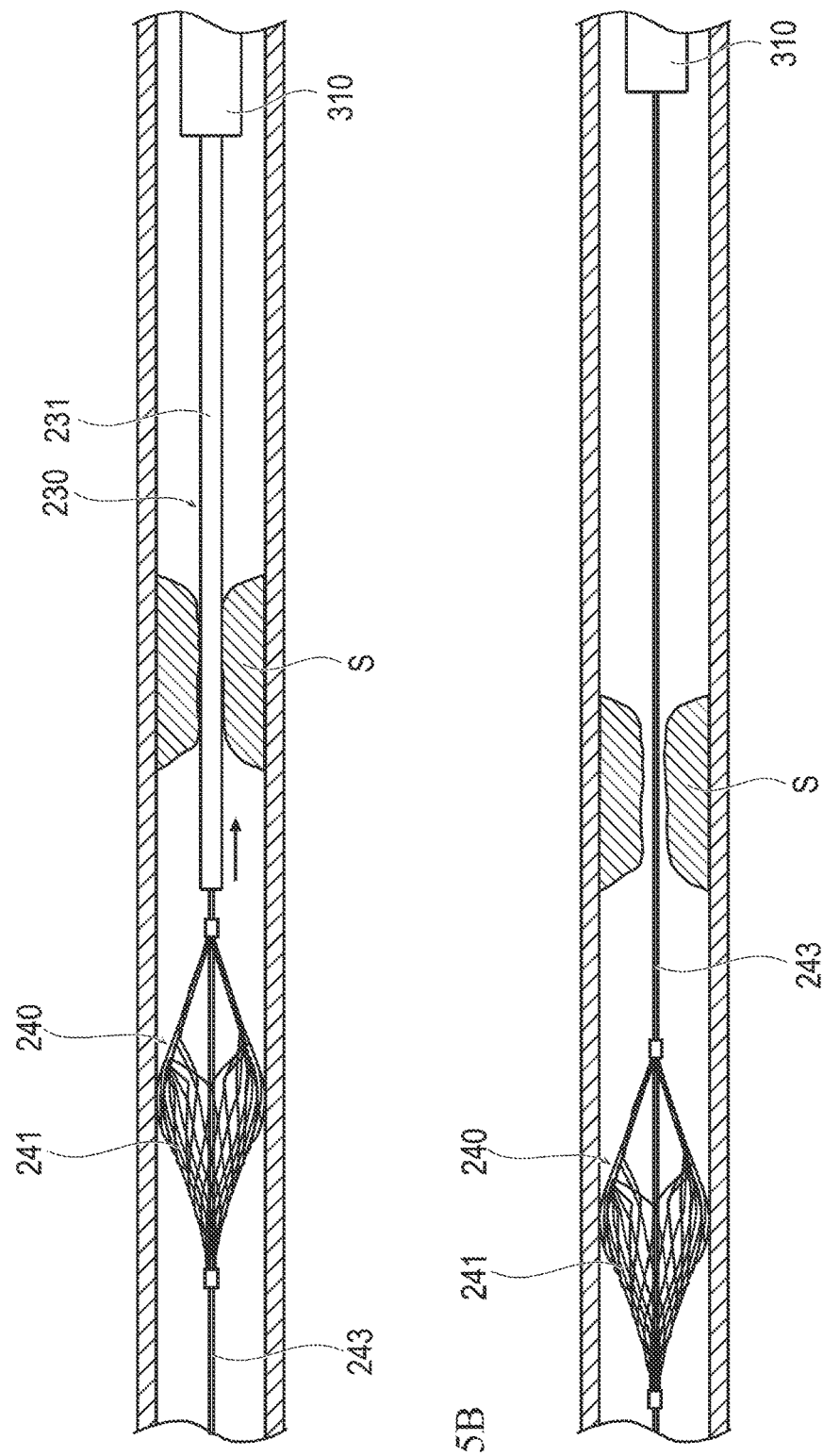

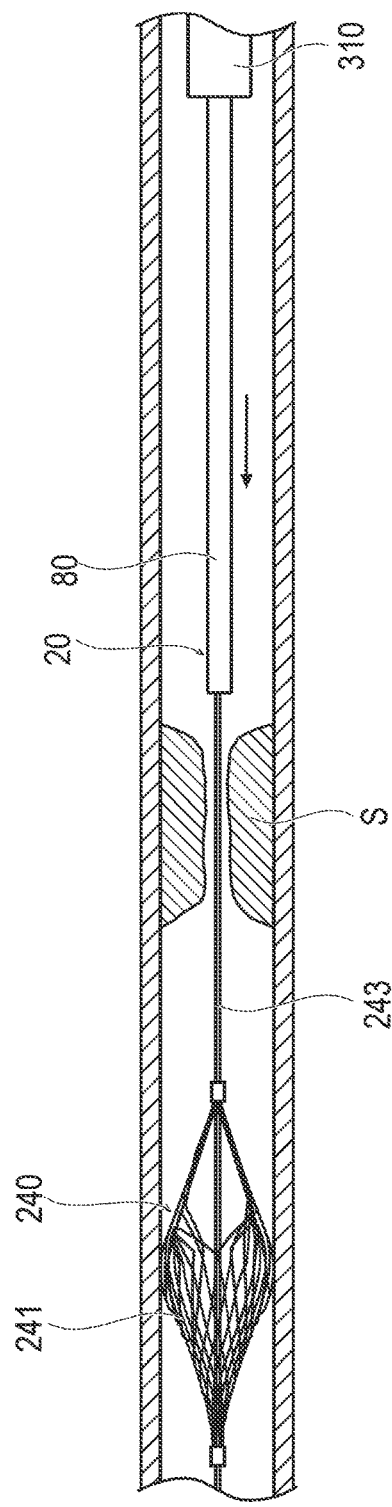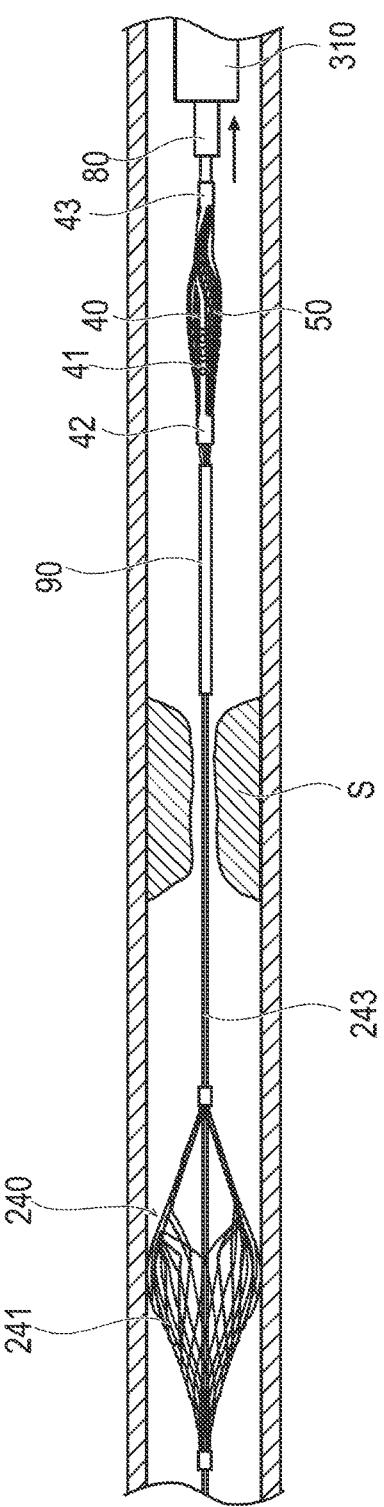
FIG. 19A
FIG. 19B

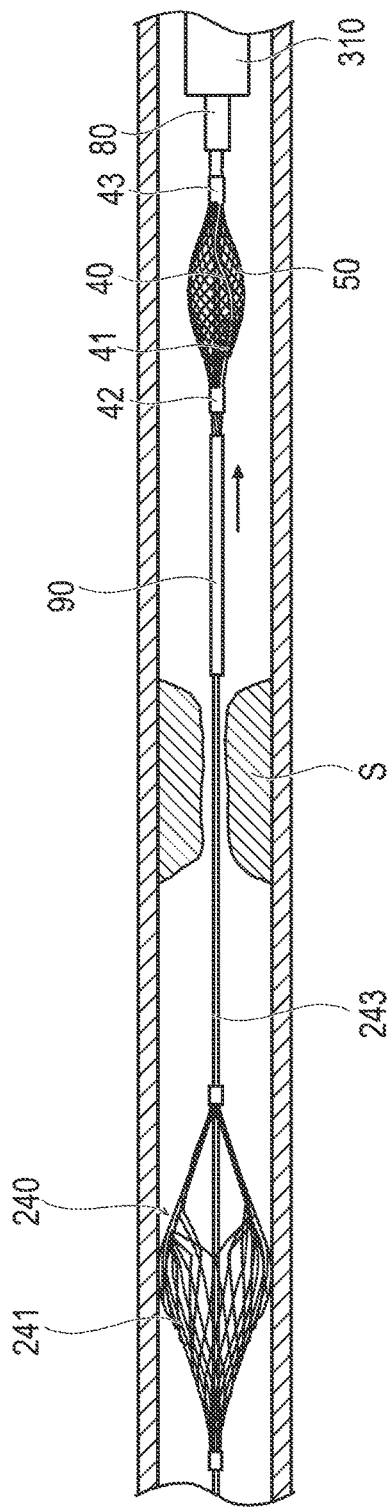
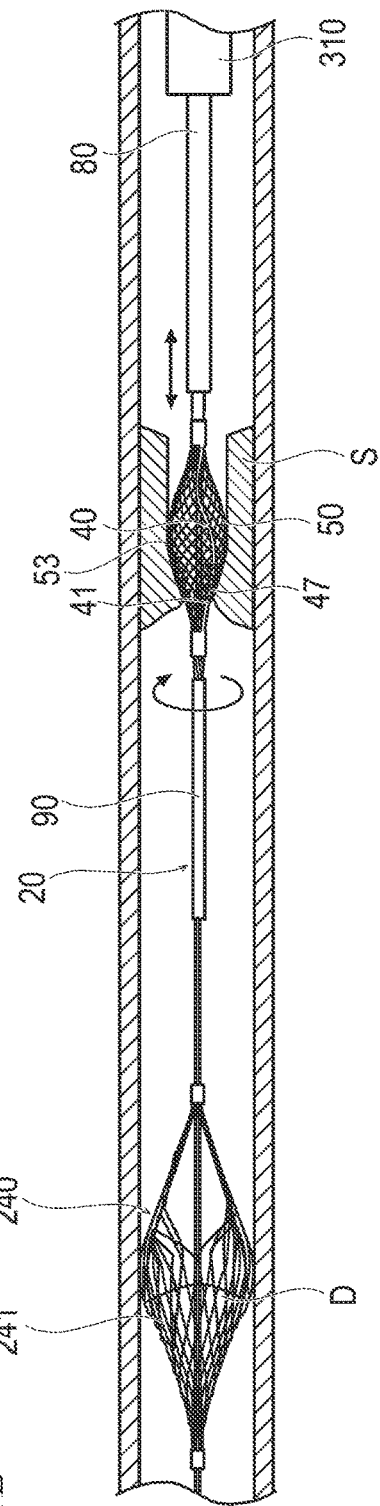
FIG. 21A
FIG. 21B

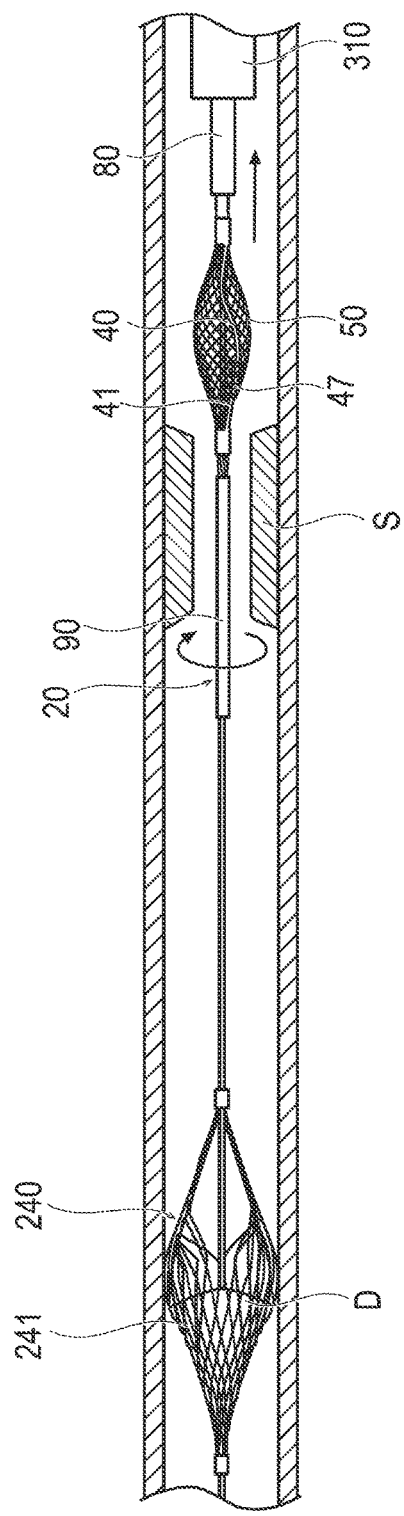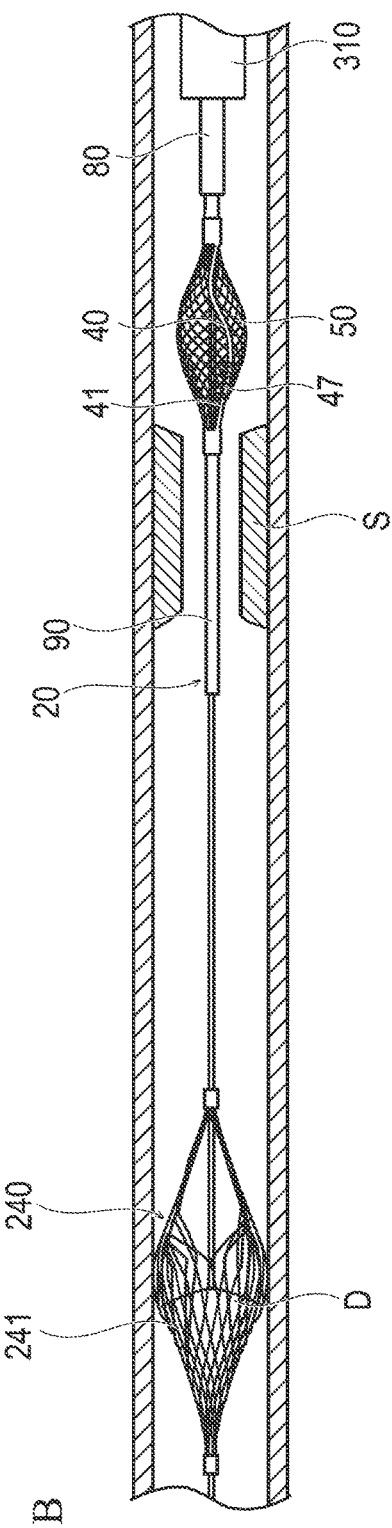
FIG. 23A
FIG. 23B

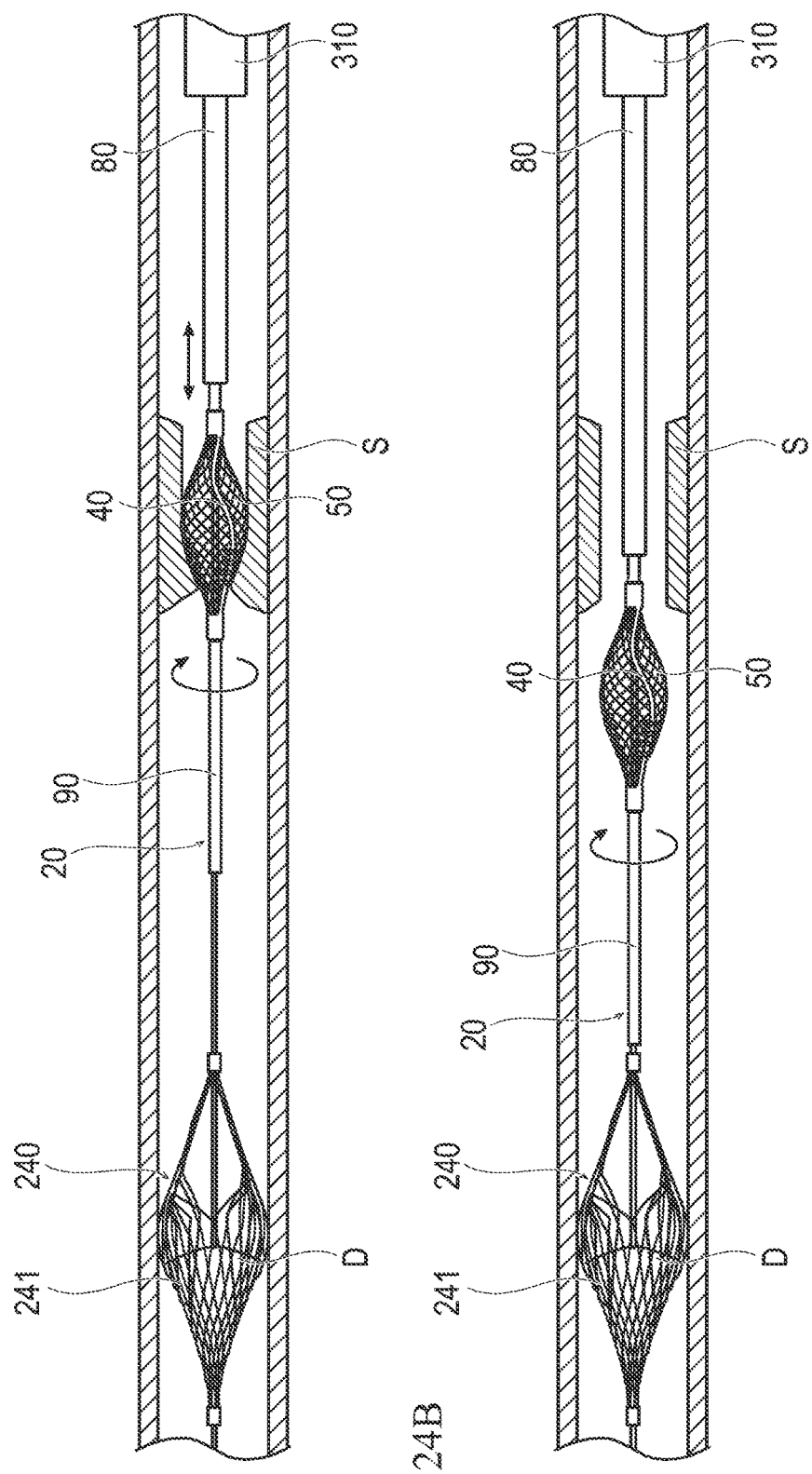

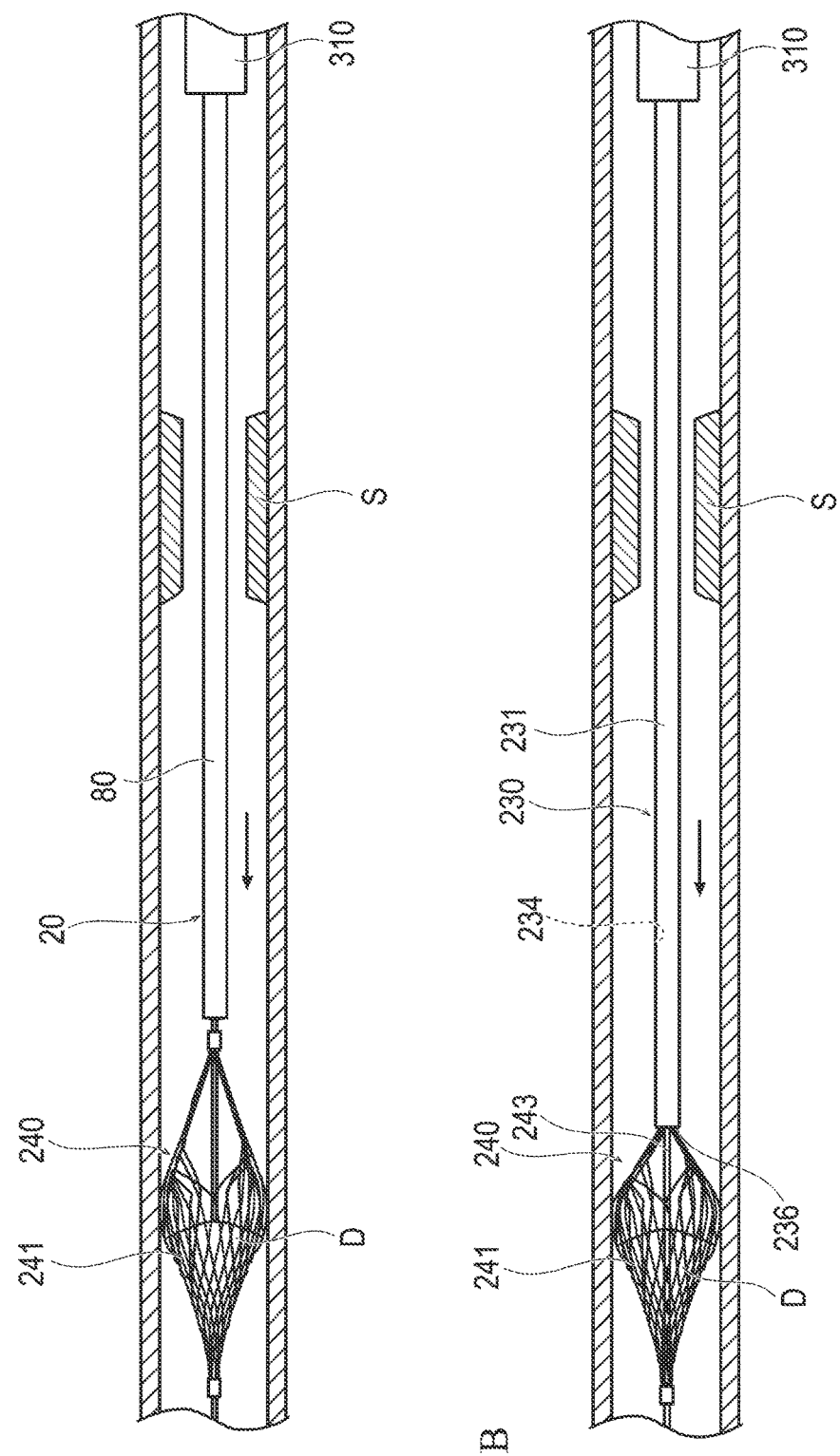

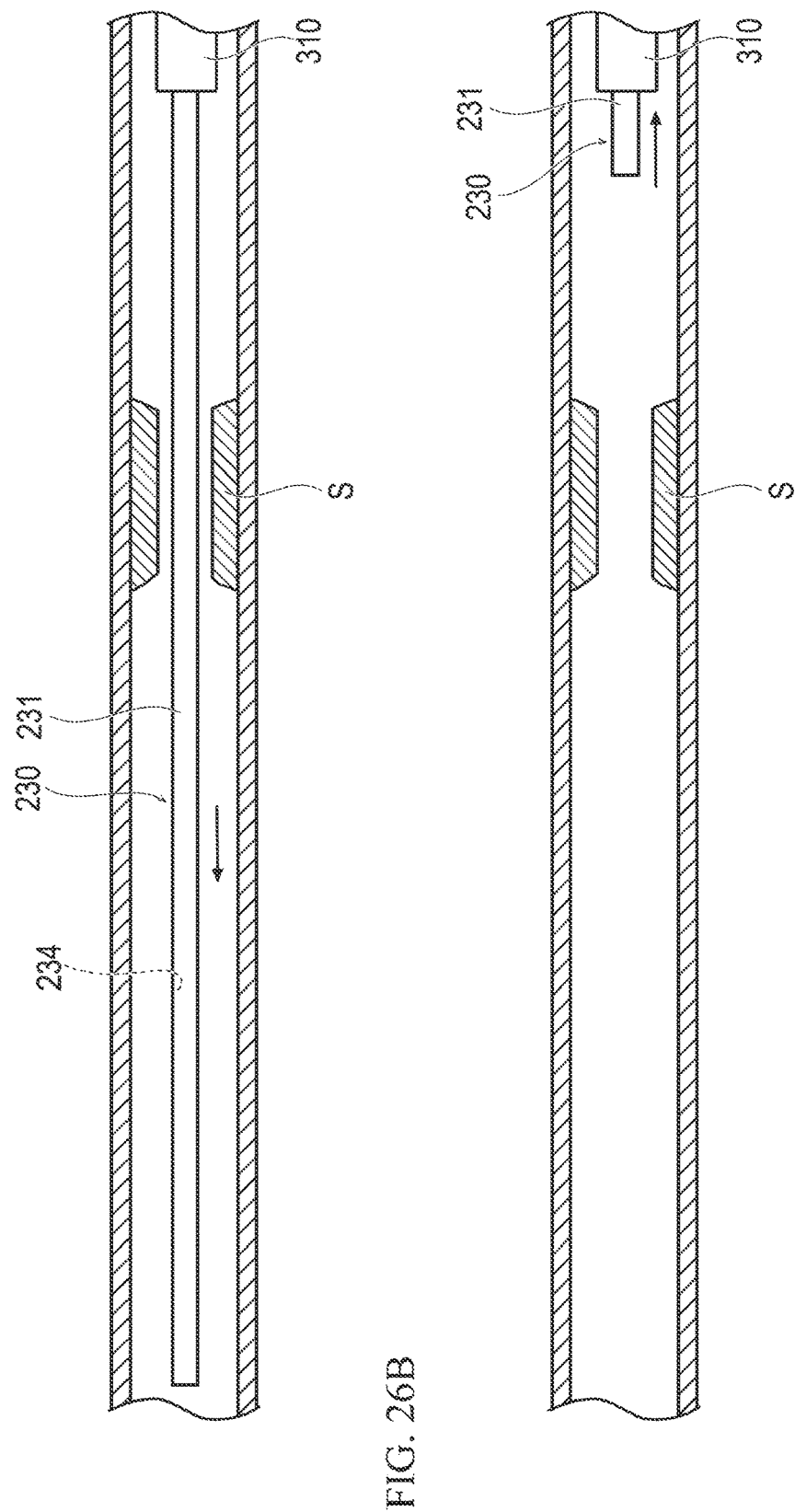

MEDICAL DEVICE

CROSS-REFERENCES TO RELATED APPLICATIONS

This application claims priority to Japanese Application No. 2015-112096 filed on Jun. 2, 2015, the entire content of which is incorporated herein by reference.

TECHNICAL FIELD

The present invention relates to a medical device which incises a substance inside a biological lumen.

BACKGROUND DISCUSSION

As a therapeutic method for a stenosed site occurring due to plaque, a thrombus, or the like in a coronary artery, it is possible to utilize percutaneous transluminal coronary angioplasty (PTCA) (in which a blood vessel is caused to expand by using a balloon), a method in which a ramified or coiled stent indwells in a blood vessel as a support for the blood vessel, and the like. However, it is difficult to apply the above-referenced methods when plaque in a stenosed site is calcified and hardened or when a stenosed site occurs in a bifurcated portion of a coronary artery. Even in such a case (i.e., when plaque in a stenosed site is calcified and hardened or in a bifurcated portion of a coronary artery), atherectomy is a therapeutic method for incising a stenotic substance such as plaque, a thrombus, and the like that can be performed.

Japanese Patent Application Publication No. JP-T-2003-504090 discloses a device for atherectomy in which diamond particles (polishing materials) adhere to an outer surface of a rotary body in the tip portion (i.e., distal-most end) of a catheter. A stenotic substance is incised (i.e., cut out or removed) by rotating the rotary body inside a coronary artery. The rotary body of the device includes four bars arranged in a circumferential direction. When the bars are flexed to protrude radially outward, the rotary body can expand so as to fit a vascular diameter. This atherectomy device includes a linear motion shaft, which is movable relative to a tubular drive shaft in an axial direction in order to cause the bars to expand, inside the drive shaft which transmits drive force to the bars performing incision.

SUMMARY

In a device disclosed in Japanese Patent Application Publication No. JP-T-2003-504090, since the linear motion shaft disposed inside the drive shaft is movable relative to the drive shaft, blood is likely to flow into a space between the drive shaft and the linear motion shaft due to blood pressure. Therefore, a seal member, for example, is needed in proximal portions of the drive shaft and the linear motion shaft to maintain liquid-tight properties. However, when the seal member is provided, a loss of the drive force occurs due to friction. Thus, it may be difficult to exhibit efficient drive at low torque.

The medical device and method disclosed here have been designed in consideration of the above-described problems. An object of the medical device disclosed here is to be insertable into a biological lumen, to be able to incise a substance inside the biological lumen, and to be drivable at low torque while maintaining liquid-tight properties between two shafts which are movable relative to one another in an axial direction.

In order to achieve this object, the medical device disclosed here is configured to incise a substance inside a biological lumen. The medical device includes: a tubular drive shaft that is rotatable; at least one strut that is interlocked with a distal side of the drive shaft in a rotatable manner, extends along a rotary axis, and is expandable radially outward in response to flexure of an intermediate portion; a tubular linear motion shaft that is disposed inside the drive shaft, is movable relative to the drive shaft in an axial direction to cause the strut to expand, and is rotatable together with the drive shaft; and a tubular interlock portion that interlocks a proximal portion of the drive shaft and a proximal portion of the linear motion shaft with each other while maintaining liquid-tight properties and is stretchable in the axial direction.

According to the medical device having the above described configuration, there is provided the stretchable interlock portion interlocking the proximal portion of the drive shaft and the proximal portion of the linear motion shaft with each other while maintaining liquid-tight properties. Therefore, the struts can expand and the substance can be incised in accordance with movement of the linear motion shaft in the axial direction with respect to the drive shaft. Moreover, liquid-tight properties between the drive shaft and the linear motion shaft can be maintained without adopting the seal member because of the tubular interlocking member. Since friction is unlikely to be generated, the medical device can be driven at low torque.

In addition, the linear motion shaft receives a rotary force not only from the distal side interlocked with the struts but also from the proximal side by (i.e., through) the interlock portion. Therefore, the linear motion shaft is likely to rotate while following the drive shaft without delay, and thus torsion imparted on the linear motion shaft is prevented. When torsion of the linear motion shaft can be prevented, the work for distorting the linear motion shaft is no longer necessary, and the drive force can be effectively transmitted. Thus, the medical device can be driven at low torque.

The interlock portion may be configured to be provided on the proximal side from a portion receiving a rotary drive force of the drive shaft. Accordingly, the interlock portion is positioned outside the human body/living body during the procedure. Therefore, safety can be ensured even if the interlock portion breaks.

The interlock portion may be configured to include a plurality of members (i.e., multiple materials/parts). This increases the design freedom of the interlock portion. It is thus possible to obtain high torque transmission performance while maintaining liquid-tight properties and stretching properties.

The interlock portion may be configured to tolerate torsion in the rotation direction between the proximal portion of the drive shaft and the proximal portion of the linear motion shaft. Accordingly, the interlock portion can absorb the misalignment in the rotation direction occurring between the linear motion shaft and the drive shaft, by being distorted. The interlock portion can thus promote smooth and natural rotations.

The interlock portion may be configured to be a pipe body (i.e., tubular) which tapers in a direction toward the proximal side. Accordingly, while maintaining liquid-tight properties between the drive shaft and the linear motion shaft, the interlock portion can smoothly and naturally interlock the drive shaft and the linear motion shaft having outer diameters different from each other.

The medical device may be configured to further have an inner tube which is a pipe body disposed inside the tubularly-formed linear motion shaft and of which rotation is not restrained with respect to the drive shaft and the linear motion shaft. Accordingly, even though the drive shaft and the linear motion shaft rotate, the inner tube does not rotate, and no rotary force acts on the wire and the like inserted into the inner tube. Therefore, in the medical device, abrasion of the wire and the like inserted into the inner tube can be prevented, and the wire and the like can be prevented from rotating and being unlikely to be pulled out. In addition, since the inner tube does not rotate, blood is unlikely to be drawn into the lumen of the inner tube. Therefore, coagulation of blood inside the lumen is inhibited from occurring, and thus, deterioration of the operability can be prevented. Since the inner tube in which the wire and the like are inserted does not rotate, the wire and the like can be prevented from receiving friction force from the inner tube and moving in the axial direction. Damage to the blood vessel can thus be prevented.

BRIEF DESCRIPTION OF DRAWINGS

FIG. 3A illustrates a state where the incision section is accommodated in an outer sheath, FIG. 3B illustrates a state where the contracted incision section protrudes from the outer sheath, and FIG. 3C illustrates a state where the incision section protruding from the outer sheath expands.

FIG. 7A is a cross-sectional view taken along line B-B in FIG. 3C, and FIG. 7B is a cross-sectional view taken along line C-C in FIG. 3C.

FIGS. 11A and 11B are longitudinal sectional views illustrating the treatment device. FIG. 11A illustrates a view before a tip tube comes into contact with the incision section, and FIG. 11B illustrates a view after the tip tube comes into contact with the incision section.

FIG. 13A illustrates a state where a guide wire is inserted into a blood vessel, and FIG. 13B illustrates a state where a guiding catheter is inserted into a blood vessel.

FIGS. 14A and 14B are schematic sectional views illustrating a state inside a blood vessel when the procedure is performed. FIG. 14A illustrates a state where a support catheter is inserted into a stenosed site, and FIG. 14B illustrates a state where the filter device is inserted into a blood vessel.

FIGS. 15A and 15B are schematic sectional views illustrating a state inside a blood vessel when the procedure is performed. FIG. 15A illustrates a state where a filter portion expands, and FIG. 15B illustrates a state immediately before the treatment device is inserted into a blood vessel.

FIGS. 19A and 19B are schematic sectional views illustrating a state inside a blood vessel when the procedure is performed. FIG. 19A illustrates a state where the treatment device is inserted into a blood vessel, and FIG. 19B illustrates a state where the incision section and a support section of the treatment device are exposed.

FIGS. 21A and 21B are schematic sectional views illustrating a state inside a blood vessel when the procedure is performed. FIG. 21A illustrates a state where the incision section and the support section expand, and FIG. 21B illustrates a state where a stenotic substance is being incised by the treatment device.

FIG. 22A illustrates a state where the incision section and the support section are pulled back from a stenosed site, and FIG. 22B illustrates a state where a stenotic substance has been incised by the treatment device.

FIGS. 23A and 23B are schematic sectional views illustrating a state inside a blood vessel when the procedure is performed. FIG. 23A illustrates a state where the incision section and the support section are pulled back from a stenosed site, and FIG. 23B illustrates a state where the incision section and the support section further expand.

FIGS. 24A and 24B are schematic sectional views illustrating a state inside a blood vessel when the procedure is performed. FIG. 24A illustrates a state where a stenotic substance is being incised by the treatment device, and FIG. 24B illustrates a state where a stenotic substance has been incised by the treatment device.

FIGS. 25A and 25B are schematic sectional views illustrating a state inside a blood vessel when the procedure is performed. FIG. 25A illustrates a state where the incision section is accommodated in the outer sheath, and FIG. 25B illustrates a state where the filter portion is accommodated inside a pipe body.

FIGS. 26A and 26B are schematic sectional views illustrating a state inside a blood vessel when the procedure is performed. FIG. 26A illustrates a state where the filter portion is accommodated inside the pipe body, and FIG. 26B illustrates a state where the medical device is evulsed.

DESCRIPTION OF EMBODIMENTS

Figure 1:
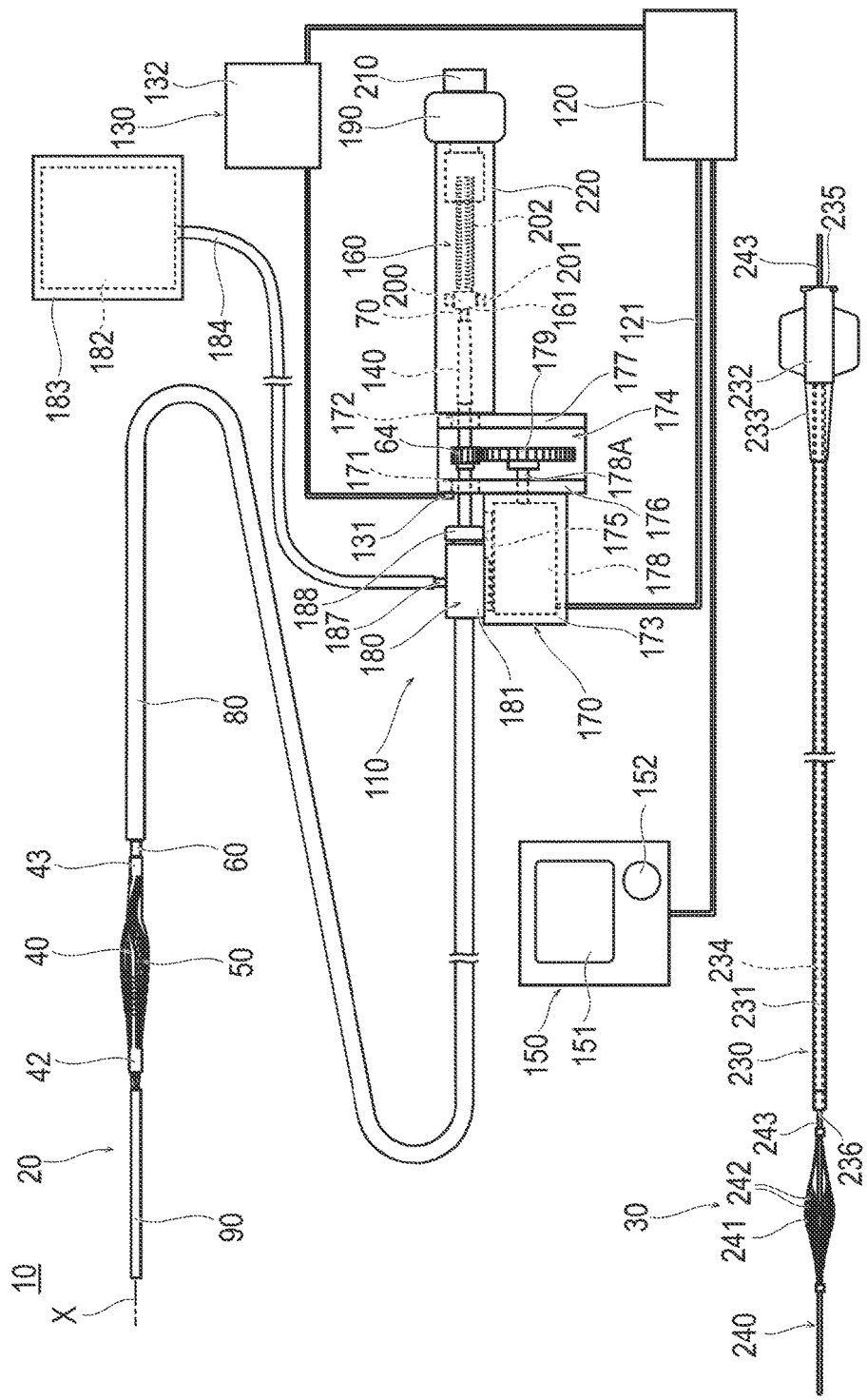
FIG. 1 is a plan view illustrating a state where an incision section of a medical device of an embodiment contracts.
Figure 2:
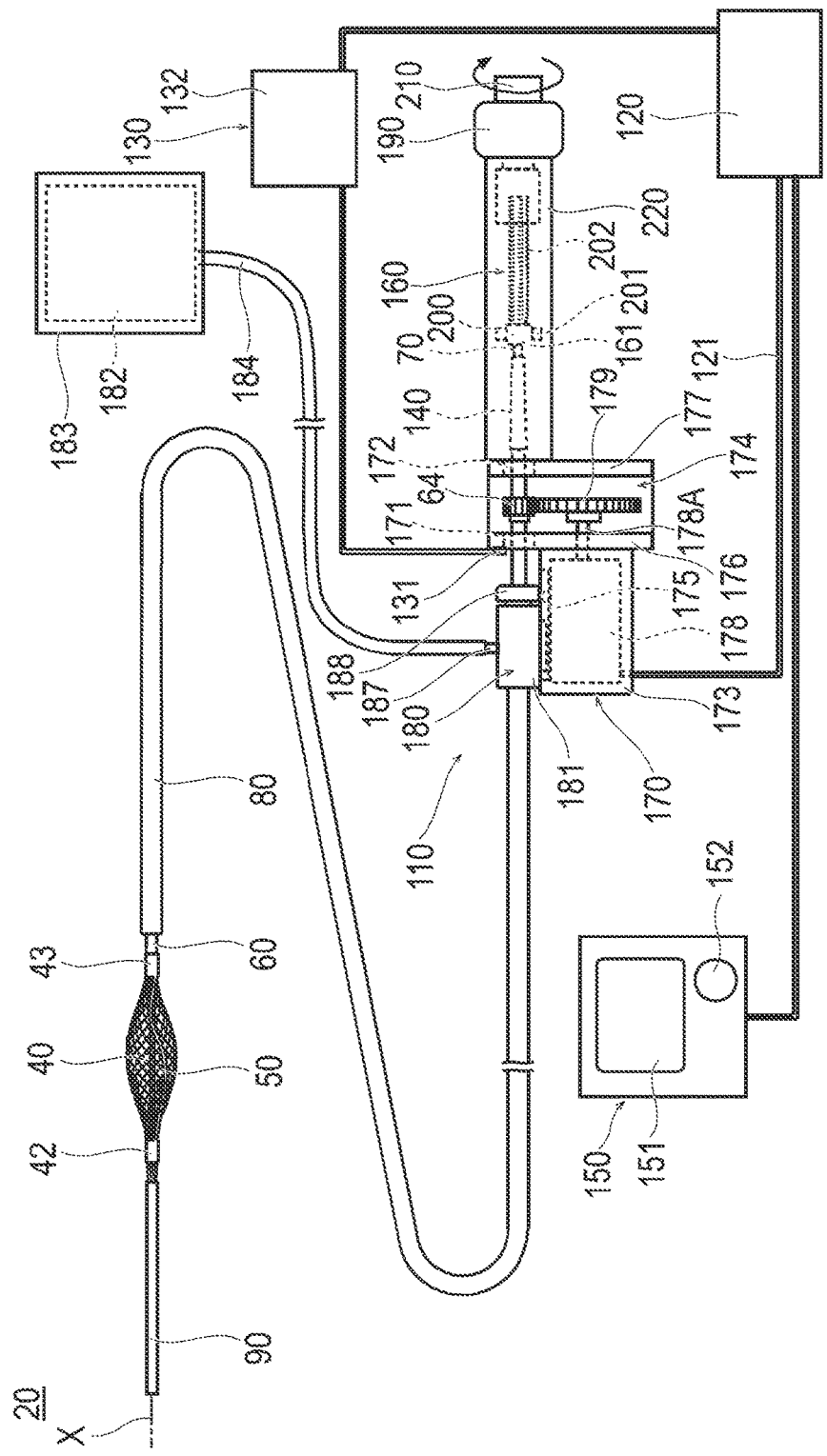
FIG. 2 is a plan view illustrating a state where the incision section of a treatment device expands.
Figure 3:
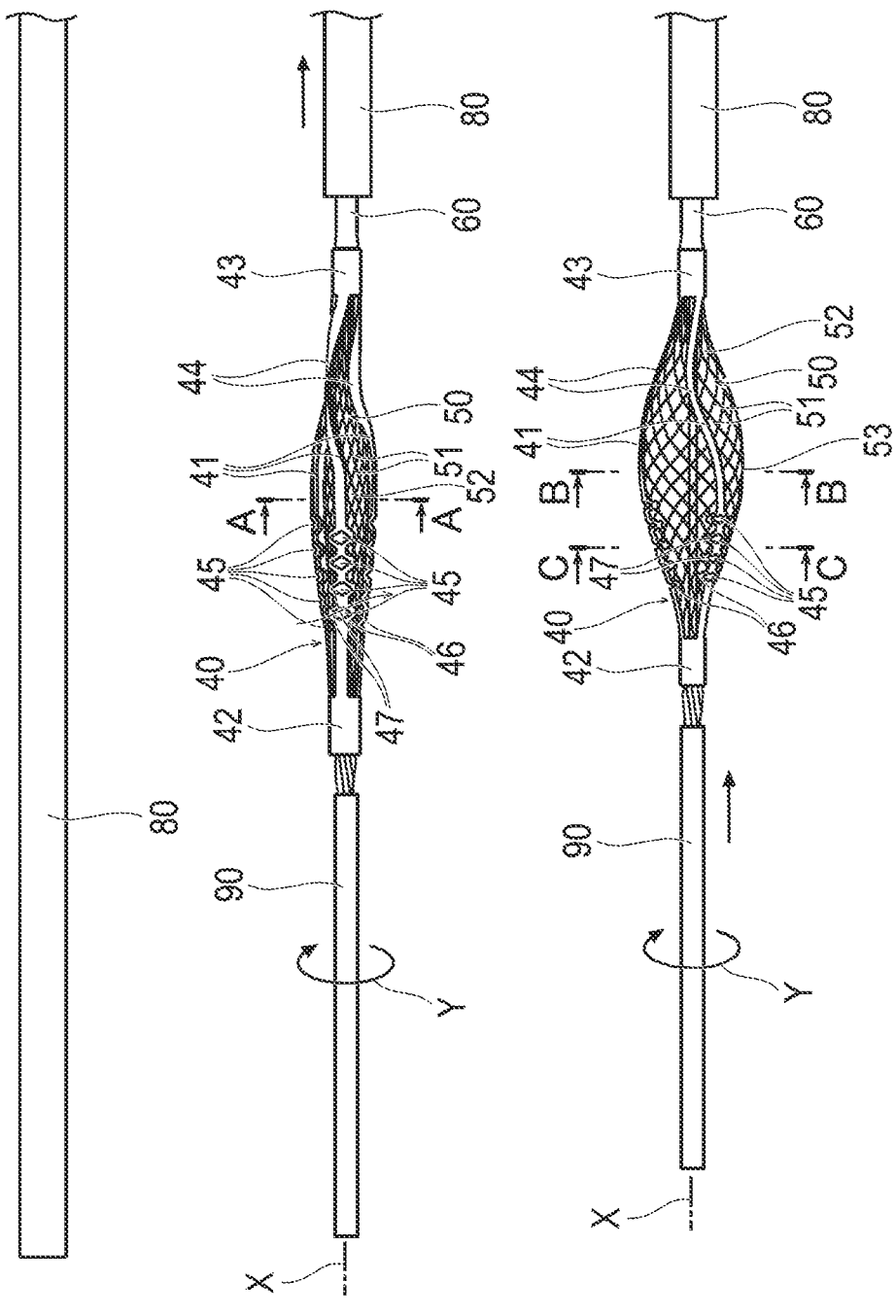
FIGS. 3A-3C are plan views illustrating a distal portion of the treatment device.

Hereinafter, with reference to the drawings, an embodiment of invention medical device and method, representing examples of the inventive medical device and method disclosed here, will be described. The disclosed medical device and method are not limited only to the following embodiments. Note that, the dimensional ratios in the drawings may be exaggerated for the convenience of description/illustration so that the dimensional ratios depicted may be different from the actual ratios.

A medical device 10 of the embodiment disclosed here is used in therapy (treatment) of incising a stenosed site or an occlusion site which is caused by plaque, a thrombus, and the like inside a blood vessel. Note that, in the present description, a side or end of the device inserted into a blood vessel will be referred to as "the distal side" or "the distal end" and a hand-side or end to be operated will be referred to as "the proximal side" or "the proximal end".

As illustrated in FIG. 1, the medical device 10 includes a treatment device 20 which incises a stenosed site or an occlusion site, and a filter device 30 which captures fallen debris (substance) scraped off from the stenosed site or the occlusion site.

As illustrated in FIGS. 2 to 5, the treatment device 20 includes an incision section 40 which can expand radially outward and contract (i.e., the incision section 40 is expandable and contractible in the radial direction), a support section 50 which supports the incision section 40, a drive shaft 60 which rotates the incision section 40 (i.e., the drive shaft 60 is configured to rotate the incision section 40), and a linear motion shaft 70 which adjusts the deformation quantity of the incision section 40 (i.e., the linear motion shaft 70 is configured to adjust the incision section 40 to control the amount of deformation). Moreover, the treatment device 20 includes a tip tube 90 which is interlocked with (i.e., fixedly connected to) a distal side of the linear motion shaft 70, an outer sheath 80 which can accommodate the incision section 40, an inner tube 100 which is disposed inside the linear motion shaft 70, and an operation unit 110 which is provided on the hand-side to be operated. Furthermore, the treatment device 20 includes a control unit 120 which controls driving of the drive shaft 60, a push-pull resistance measurement unit 130 which is attached to the drive shaft 60, an interlock portion 140 which interlocks the drive shaft 60 and a proximal portion of the linear motion shaft 70 with each other, and a notification unit 150 notifies a user that the incision resistance exceeds a threshold value.

As illustrated in FIGS. 3A to 3C, 4, 6, 7A, and 7B, the incision section 40 includes at least one of a plurality of struts 41 (four in the present embodiment) which extend along a rotary axis "X" of the drive shaft 60 (i.e., the longitudinal axis that the drive shaft 60 rotates about), a tubular distal end portion 42 which is integrally formed with the struts 41 on the distal side of all of the struts 41, and a tubular proximal fixing end 43 which is integrally formed with the struts 41 on the proximal side of all of the struts 41. The distal end portion 42 is not fixed to the support section 50 and the linear motion shaft 70, but is movable relative to the support section 50 and the linear motion shaft 70 in an axial direction (i.e., the distal end portion 42 is a free end). When the linear motion shaft 70 moves proximally (i.e., in a direction toward the proximal side) relative to the incision section 40, the distal end portion 42 comes into contact with a proximal portion of the tip tube 90 which is interlocked with the linear motion shaft 70 (as illustrated in FIGS. 11A and 11B).

Each strut 41 includes an inclination portion 44 on its proximal side and is curved so as to incline with respect to the rotary axis X in a contraction state (i.e., when the strut 41 is contracted). Each strut 41 also includes a plurality of opening portions 45 on its distal side that penetrate the strut 41 from the outer peripheral surface to the inner peripheral surface (i.e., each opening portion 45 is a through-hole or thru-hole in the strut 41). Each strut 41 has wide width portions 46 that each possess a width in the circumferential direction (rotation direction "Y") relatively wider than an adjacent portion of the strut 41. The opening portions 45 are respectively formed in the wide width portions 46. The plurality (four or five in the present embodiment) of opening portions 45 are formed along the extending direction (i.e., axial direction) of each strut 41. An inner edge portion of each opening portion 45 functions as a blade 47 which incises a stenosed site or an occlusion site. The blades 47 of the struts 41 are formed at positions on the distal side from the portion in which the outer diameter formed with the struts 41 in the expansion state is maximized (a substantially intermediate portion in a direction along the rotary axis X). In other words, the blades 47 are located distally of the midpoint of the struts 41. In the struts 41, it is preferable that any edge portions other than the inner edge portions (configured to be the blades 47 of the opening portions 45) are chamfered.

One strut 41 having four opening portions 45 and another strut 41 having five opening portions 45 are alternately disposed in the circumferential direction (i.e., struts 41 with four opening portions 45 alternate with struts with five opening portions 45 in the circumferential direction). Therefore, when the incision section 40 is cut out from one pipe body through laser processing, machining processing, or the like, the four opening portions 45 and the five opening portions 45 can be alternately disposed one by one, and thus, it is possible to ensure appropriate widths of the opening portions 45. In addition, when the blades 47 of each strut 41 are respectively misaligned with those of an adjacent strut 41 in the circumferential direction, a predetermined portion is prevented from being biasedly scraped off, and thus, it is possible to effectively incise (i.e., cut out a portion of) a stenosed site or an occlusion site.

Figure 7A:
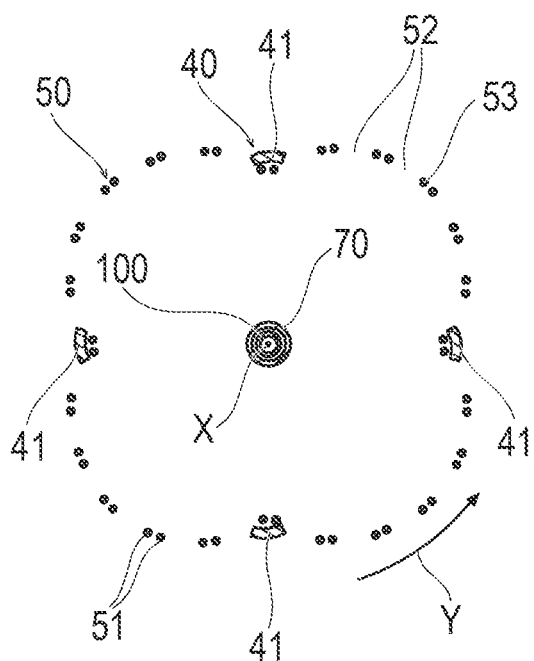
FIGS. 7A and 7B are views illustrating the treatment device in an expansion state.
Figure 7B:
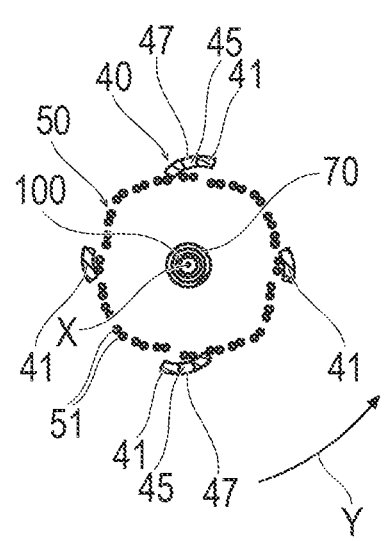

When the struts 41 are in the expansion state, the outer peripheral surface of the portion having the blades 47 is deformed to incline radially inward, toward the rotation direction Y side (refer to FIG. 7B). Therefore, when rotating in the expansion state, the struts 41 smoothly come into contact with a contact target from the sides of the struts 41 inclining radially inward. Accordingly, it is possible to reduce excessive damage to biological tissue. In addition, since the struts 41 are formed by being cut out from a pipe body having a diameter smaller than the diameter of the struts 41 in the expansion state, the radius of curvature of the outer peripheral surface of each strut 41 is smaller than the distance from the rotary axis "X" to the outer peripheral surface of the strut 41 in the expansion state. Therefore, the edge portions of the struts 41 are less likely to come into contact with the contact target, and it is thus possible to further reduce excessive damage to biological tissue.

The material of the incision section 40, for example, may be a shape memory alloy in which a shape memory effect and super-elasticity are applied through heat treatment, stainless steel, and the like. The shape memory alloy may preferably be a Ni—Ti-based alloy, a Cu—Al—Ni-based alloy, a Cu—Zn—Al-based alloy, a combination of alloys, or the like.

The support section 50 provides radially inward support to the incision section 40. The support section 50 is tubularly formed with a plurality of braided wire materials 51. The braided wire materials 51 overlap to form apertures 52 among the wire materials 51. In a distal side end portion 54 of the support section 50, the plurality of wire materials 51 are gathered (i.e., concentrated) so as to form a tube (i.e., possess a tubular shape). The distal side end portion 54 of the support section is fixed to the outer peripheral surface of the linear motion shaft 70 and is unfixed relative to the inner side surface of the distal end portion 42 of the incision section (i.e., the distal side end portion 54 is not fixed to the distal end portion 42). In a proximal side end portion 55 of the support section 50, the plurality of wire materials 51 are gathered so as to form a tube shape. The proximal side end portion 55 is fixed to the inner peripheral surface of the proximal fixing end 43 of the struts 41.

In a maximum expansion portion 53 of the support section 50 of which the outer diameter is maximized in the expansion state (i.e., the portion of the support section 50 possessing the largest outer diameter when the support section 50 is in the expansion state), gaps among the struts 41 (i.e., gaps between adjacent struts 41) are widened in the expansion state. Therefore, the maximum expansion portion 53 protrudes radially outward between the struts 41 as illustrated in FIG. 7A (the maximum expansion portion 53 protrudes beyond the struts 41 such that the maximum expansion portion 53 possesses an outer diameter that is greater than the outer diameter of the struts 41). Therefore, the portions of the struts 41 maximally expanding outward and being likely to come into contact with biological tissue in the expansion state are positioned on the radially inner side from the maximum expansion portion 53 of the support section 50, and thus, normal biological tissue can be prevented from being damaged by the edge portions of the struts 41. In other words, the support section 50 extends radially outward more than the struts 41 so that the support section 50 will contact the biological tissue before the struts 41 contact the biological tissue to prevent the edge portions of the struts 41 from damaging the biological tissue.

Since the distance to the portion in the vicinity of the blades 47 of each strut 41 from the rotary axis X is short (i.e., the strut is smaller in diameter at the portion in the vicinity of the blades 47 than at the maximum diameter portion) and the wide width portions 46 are formed in this portion of the struts 41, the gaps between the struts 41 are narrow (i.e., more narrow than at the maximum diameter portion). Therefore, the support section 50 positioned in the vicinity of the blades 47 is prevented from protruding radially outward among the struts 41 (i.e., the struts 41 possess a larger outer diameter than the support section 50 in the portion at the vicinity of the blades 47 because the support section 50 is prevented from protruding radially outward beyond the struts 41). Thus, the blades 47 can come into contact with the contact target without being hindered by the support section 50 (refer to FIG. 7B).

In order to avoid damage to biological tissue, it is preferable that the wire materials 51 forming the support section 50 be less rigid than the struts 41. The wire materials 51 forming the support section 50 also preferably possess corner portions in the cross section formed to have curvatures (i.e., the cross-section of each of the wire materials 51 includes curves), and it is more preferable that the cross section is formed to have a circular shape.

The outer diameter of each wire material 51 can be suitably selected depending on the material, application conditions, and the like of the wire materials 51. For example, the outer diameter of each wire material 51 may range from 0.05 mm to 0.15 mm.

It is preferable that the wire material 51 is a flexible material. For example, it is possible to favorably use a shape memory alloy in which a shape memory effect and superelasticity are applied through heat treatment; stainless steel; Ta; Ti; Pt; Au; W; polyolefin such as polyethylene, polypropylene, and the like; polyamide; polyester such as polyethylene terephthalate and the like; a fluorine-based polymer such as ETFE and the like; PEEK (polyether ether ketone); polyimide; and the like. The shape memory alloy preferably is a Ni—Ti-based alloy, a Cu—Al—Ni-based alloy, a Cu—Zn—Al-based alloy, a combination of alloys, or the like. As a structure in which a plurality of materials are combined together, for example, it is possible to exemplify a structure in which a core wire made from Pt is coated with a Ni—Ti alloy in order to apply contrast properties, and a structure in which a core wire made from a Ni—Ti alloy is subjected to gold plating.

The inner diameter of the incision section 40 in the contraction state can be suitably selected in accordance with the inner diameter and the like of a biological lumen in which the incision section 40 is to be applied. For example, the inner diameter of the incision section 40 may range from 0.9 mm to 1.6 mm. As an example, the inner diameter of the incision section 40 can be set to 1.4 mm. The outer diameter of the incision section 40 in the contraction state can be suitably selected in accordance with the inner diameter and the like of a biological lumen in which the incision section 40 is to be applied. For example, the outer diameter of the incision section 40 may range from 1.1 mm to 1.8 mm. As an example, the outer diameter of the incision section 40 can be set to 1.7 mm. The length of the incision section 40 in the direction along the rotary axis "X" can be suitably selected in accordance with the length and the like of a biological lumen in which the incision section 40 is to be applied. For example, the length of the incision section 40 may range from 10 mm to 30 mm. As an example, the length of the incision section 40 can be set to 20 mm.

The maximum outer diameter of the incision section 40 in the expansion state can be suitably selected in accordance with the inner diameter and the like of a biological lumen in which the incision section 40 is to be applied. For example, the maximum outer diameter of the incision section 40 may range from 3.0 mm to 8.0 mm. As an example, the maximum outer diameter of the incision section 40 can be set to 7.0 mm.

The length of the maximum expansion portion 53 of the support section 50 in the expansion state protruding radially outward from the struts 41 can be suitably set. For example, the protrusion length of the maximum expansion section 43 (i.e., the distance that the maximum expansion section 43 protrudes radially outward beyond the struts 41) may range from 0.05 mm to 0.5 mm. As an example, the protrusion length of the maximum expansion portion 53 can be set to 0.2 mm.

A portion of the plurality of wire materials 51 (e.g., one wire material out of the plurality of wire materials 51) may be a wire material having X-ray contrast properties. Accordingly, the positions and the expansion diameters of the support section 50 and the incision section 40 can be precisely grasped under radioscopy, and thus, the procedure is further facilitated (i.e., operability is improved). As the material having X-ray contrast properties, for example, gold, platinum, a platinum-iridium alloy, silver, stainless steel, molybdenum, tungsten, tantalum, palladium, an alloy thereof, and the like are favorable. Note that a portion of the incision section 40 may be made from a material having X-ray contrast properties instead of a portion of the support section 50. For example, the inner peripheral surface of the incision section 40 may be coated with a material having X-ray contrast properties through plating processing. Accordingly, the positions and the expansion diameters of the support section 50 and the incision section 40 can be precisely grasped under radioscopy, and thus, the procedure is further facilitated (i.e., operability is improved).

Figure 4:
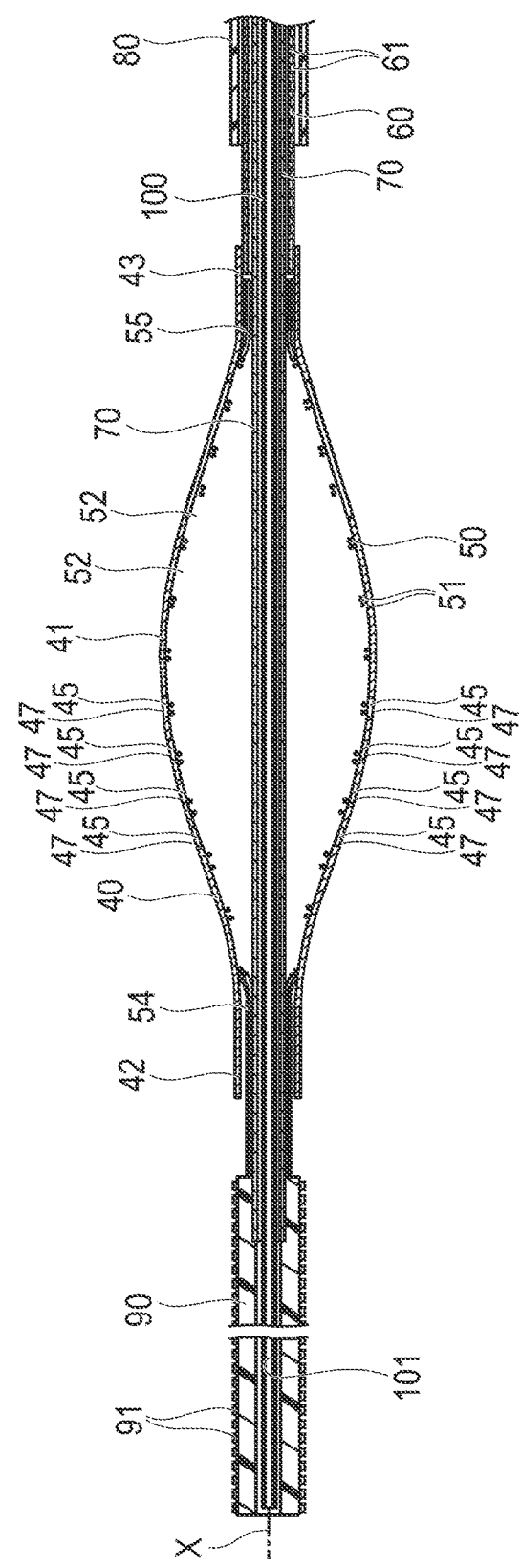
FIG. 4 is a longitudinal sectional view illustrating the distal portion of the treatment device.

The support section 50 can be in the expansion state (refer to FIGS. 11A and 11B) when the intermediate portion of the support section 50 is deformed to be flexed radially outward by causing the distal side end portion 54 and the proximal side end portion 55 to be closer to each other than when in the contraction state (refer to FIG. 4 showing the tubular support section 50 having a more substantially uniform outer diameter). When the intermediate portion of the support section 50 is flexed radially outward, the distal side end portion 54 gradually approaches the tip tube 90, and the struts 41 disposed on the outer side of the support section 50 are pressed radially outward by the support section 50, thereby expanding. Until the tip tube 90 comes into contact with the distal side end portion 54, as illustrated in FIG. 11A, since the distal end portion 42 is not fixed to the support section 50 and the linear motion shaft 70, force in the axial direction seldom acts between the distal end portion 42 and the proximal fixing end 43, and the incision section 40 expands only by the radially outward force received from the support section 50. Therefore, gaps are unlikely to be generated between the struts 41 and the wire materials 51. Thus, no stenotic substance or debris is interposed among the struts 41 and the wire materials 51, the struts 41 can be prevented from being damaged, and normal biological tissue can be prevented from being damaged by the edge portions of the struts 41. When the tip tube 90 moving together with the linear motion shaft 70 comes into contact with the distal end portion 42, as illustrated in FIG. 11B, the distal end portion 42 receives force from the tip tube 90 in the direction toward the proximal side, and the tip tube 90 exerts a proximal force in the axial direction on the distal end portion 42. Accordingly, the struts 41 expand not only by the radially outward force received from the support section 50 but also by the contraction force (i.e., the distal end portion 42 moving proximally while the proximal end portion 43 remains fixed). Therefore, while maintaining a desirable state where gaps are unlikely to be generated between the struts 41 and the wire materials 51, it is possible to prevent the incision section 40 from being pressed more than necessary by the support section 50.

Figure 5:
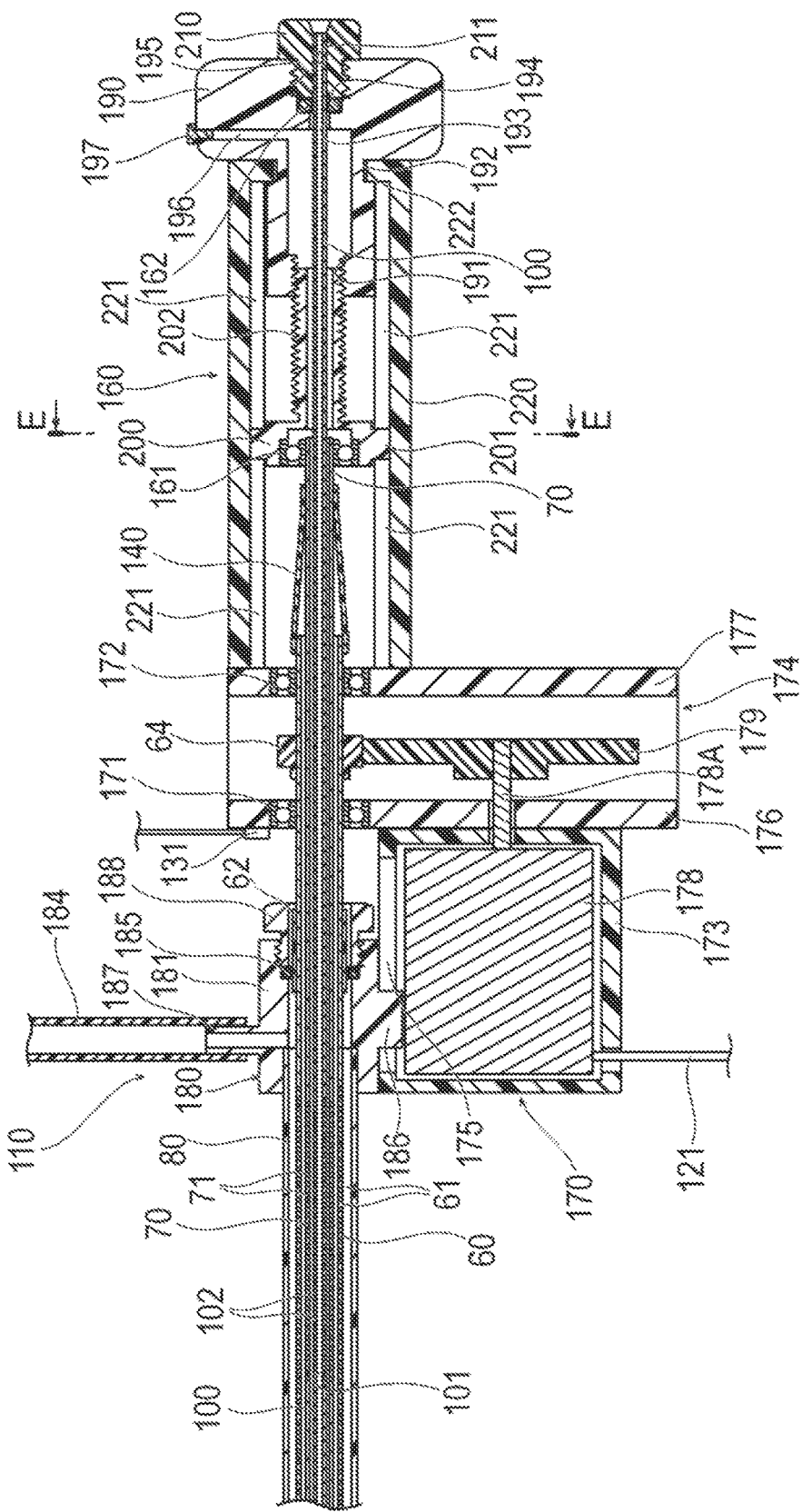
FIG. 5 is a longitudinal sectional view illustrating a proximal portion of the treatment device.
Figure 6:
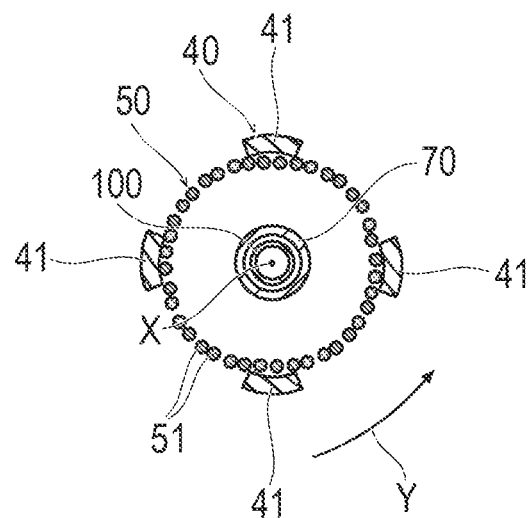
FIG. 6 is a cross-sectional view taken along line A-A in FIG. 3B.

As illustrated in FIGS. 4 and 5, the drive shaft 60 is tubularly formed. The distal side of the drive shaft 60 is fixed to the proximal fixing end 43 of the incision section 40, and a driven gear 64 is fixed to the proximal side of the drive shaft 60. In at least a portion of the drive shaft 60, a plurality of hole portions 61 through which a fluid can circulate are formed and penetrate the drive shaft 60 from the inner peripheral surface to the outer peripheral surface (i.e., the hole portions 61 are through-holes or thru-holes in the drive shaft 60). A portion on the outer peripheral surface of a proximal portion of the drive shaft 60 is coated with a coating portion 62 which slidably comes into contact with a first seal portion 185 inside the operation unit 110 and reduces the friction force between the drive shaft 60 and the first seal portion 185.

The drive shaft 60 has characteristics of being soft and being able to transmit rotary power acting from the proximal side to the distal side. For example, the drive shaft 60 is configured to be a multi-layer coiled pipe body. The drive shaft 60 may be a three-layer coil or the like in which the winding directions are alternately arranged in a right-left-right manner. The drive shaft 60 may be made from a material in which a reinforcement member such as a wire material and the like is embedded in polyolefin such as polyethylene, polypropylene, and the like; polyamide; polyester such as polyethylene terephthalate and the like; a fluorine-based polymer such as ETFE and the like; PEEK (polyether ether ketone); polyimide; and the like, or a combination of these materials.

The inner diameter of the drive shaft 60 can be suitably selected. For example, the inner diameter of the drive shaft 60 may range from 0.7 mm to 1.4 mm. As an example, the inner diameter of the drive shaft 60 can be set to 1.2 mm. The outer diameter of the drive shaft 60 can be suitably selected. For example, the outer diameter of the drive shaft 60 may range from 0.8 mm to 1.5 mm. As an example, the outer diameter of the drive shaft 60 can be set to 1.35 mm.

Figure 8:
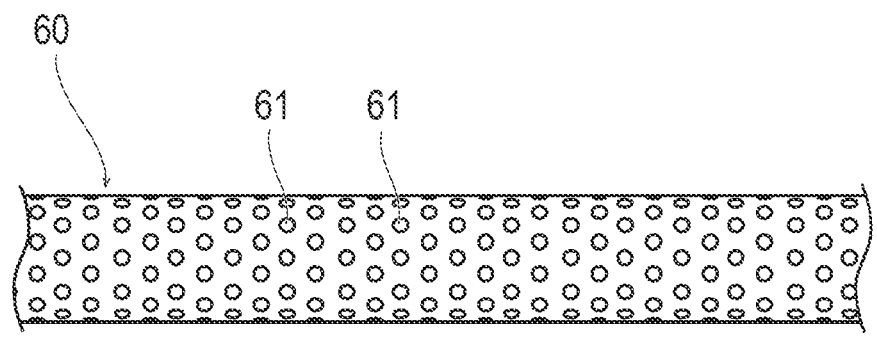
FIG. 8 is a plan view illustrating a drive shaft.
Figure 9:
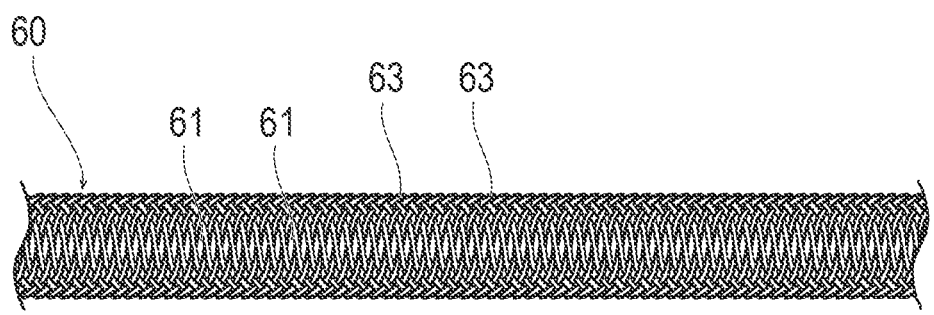
FIG. 9 is a plan view illustrating another embodiment of the drive shaft.

It is preferable that the coating portion 62 is a low-friction material, for example, a fluorine-based resin material such as polytetrafluoroethylene (PTFE) and the like. As illustrated in FIG. 8, the hole portions 61 of the drive shaft 60 may be a plurality of penetration holes which are provided in the pipe body. Otherwise, the hole portions 61 may be gaps which are formed in a braided body obtained by braiding a wire material 63 as illustrated in FIG. 9. In addition, the drive shaft 60 may be configured to be a coil, and the hole portions 61 may be gaps in the coil. The hole portions 61 may be formed in the drive shaft 60 in its entirety or may be partially formed in the drive shaft 60. The drive shaft 60 can be easily formed to have the hole portions 61 within only a predetermined range by partially coating the braided body or the coil having the gaps with a material such as a resin and the like (i.e., the not coated portion will have the hole portions 61 and the coated portion will not have the hole portions 61).

As illustrated in FIGS. 4 and 5, the linear motion shaft 70 is a pipe body which is movable relative to the drive shaft 60 in the rotary axis "X" direction (i.e., the axial direction) in order to cause the incision section 40 and the support section 50 to expand and contract. The linear motion shaft 70 penetrates the drive shaft 60, the incision section 40, and the support section 50 (i.e., the linear motion shaft 70 extends within the drive shaft 60, the incision section 40, and the support section 50). The distal side of the linear motion shaft 70 is fixed to the distal side end portion 54 of the wire materials 51, and the proximal side of the linear motion shaft 70 is connected to a movement mechanism unit 160 which moves the linear motion shaft 70 straight along the rotary axis "X" (i.e., the linear motion shaft 70 is distally and proximally movable in the axial direction). The proximal side of the linear motion shaft 70 protrudes toward the proximal side further than the drive shaft 60 (i.e., the proximal end of the linear motion shaft 70 is located proximally of the proximal end of the drive shaft 60). At least a portion of the linear motion shaft 70 possesses a plurality of hole portions 71 through which a fluid can circulate. The hole portions 71 penetrate the linear motion shaft 70 from the inner peripheral surface to the outer peripheral surface of the linear motion shaft 70 (i.e., the hole portions 71 are through-holes or thru-holes). Similar to the hole portions 61 of the drive shaft 60, the hole portions 71 of the linear motion shaft 70 may be a plurality of penetration holes provided in the pipe body. Otherwise, the hole portions 71 may be configured to be gaps in a braided body or a coil.

It is preferable that the linear motion shaft 70 is a flexible material. For example, it is possible to favorably use a shape memory alloy in which a shape memory effect and superelasticity are applied through heat treatment; stainless steel; Ta; Ti; Pt; Au; W; polyolefin such as polyethylene, polypropylene, and the like; polyamide; polyester such as polyethylene terephthalate and the like; a fluorine-based polymer such as ETFE and the like; PEEK (polyether ether ketone); polyimide; and the like. The shape memory alloy is preferably a Ni—Ti-based alloy, a Cu—Al—Ni-based alloy, a Cu—Zn—Al-based alloy, a combination of alloys, or the like. In addition, the linear motion shaft 70 may be made from a plurality of materials. A reinforcement member such as a wire material and the like may be embedded in the linear motion shaft 70.

The inner diameter of the linear motion shaft 70 can be suitably selected. For example, the inner diameter of the linear motion shaft 70 may range from 0.5 mm to 1.2 mm. As an example, the inner diameter of the linear motion shaft 70 can be set to 0.95 mm. The outer diameter of the linear motion shaft 70 can be suitably selected. For example, the outer diameter of the linear motion shaft 70 may range from 0.6 mm to 1.3 mm. As an example, the outer diameter of the linear motion shaft 70 can be set to 1.05 mm.

The interlock portion 140 is a stretchable tubular member which interlocks the proximal portion of the linear motion shaft 70 and the proximal portion of the drive shaft 60 with each other (i.e., the interlock portion 140 is connected to the outer peripheral surface of each of the proximal portions of the linear motion shaft 70 and the drive shaft 60), and which tapers in the direction toward the proximal side (i.e., tapers or possesses a decreasing outer diameter in the proximal direction). The interlock portion 140 is interlocked with the linear motion shaft 70 and the drive shaft 60 in a liquid-tight manner. While maintaining liquid-tight properties between the linear motion shaft 70 and the drive shaft 60 in the operation unit 110, the interlock portion 140 tolerates movement of the linear motion shaft 70 in the axial direction with respect to the drive shaft 60. When the linear motion shaft 70 and the drive shaft 60 (which move relative to one another) are interlocked with each other by the stretchable interlock portion 140, there is no need to employ a seal structure such as an O-ring and the like generating friction. Therefore, it is possible to maintain liquid-tight properties between the linear motion shaft 70 and the drive shaft 60 without causing loss of the drive force due to friction. In addition, the interlock portion 140 can absorb the misalignment of the linear motion shaft 70 and the drive shaft 60 in the rotation direction by being distorted (i.e., because the interlock portion is flexible and restoring its original shape).

The interlock portion 140 material is not particularly limited as long as it is a stretchable material. For example, various types of rubber materials such as natural rubber, isoprene rubber, butadiene rubber, chloroprene rubber, silicone rubber, fluorine rubber, styrene-butadiene rubber, and the like; a thermoplastic elastomer such as a styrene-based elastomer, a polyolefin-based elastomer, a polyurethane-based elastomer, a polyester-based elastomer, a polyamide-based elastomer, a polybutadiene-based elastomer, a trans-polyisoprene-based elastomer, a fluorine rubber-based elastomer, a chlorinated polyethylene-based elastomer, and the like; and the like can be favorably used.

The interlock portion 140 may also be made from a plurality of members. For example, it is possible to adopt a multi-layer structure. A member such as a coil and a spring formed from a metal wire, a braid in which a metal wire is braided, or the like having high torque transmission performance can be used for the inner layer, and a stretchable member such as the above-referenced rubber material, a thermoplastic elastomer, and the like having sealing properties can be used for the outer layer. Accordingly, rotary force of the drive shaft 60 can be more efficiently transmitted to the linear motion shaft 70. Note that, a different material such as a resin and the like may be used as the material of the inner layer without being limited to metal as long as the material has torque transmission performance and strength. In addition, the configurations of the inner and outer layers may be switched.

The outer sheath 80 is a pipe body (i.e., is tubular) covering the outer side of the drive shaft 60 and is movable in the direction along the rotary axis "X". The outer sheath 80 can be operated while the proximal portion is grabbed, can accommodate the incision section 40 and the support section 50 in the contraction state within the outer sheath 80 by moving toward the distal side (i.e., distally relative to the incision section 40 and the support section 50), and can expose the incision section 40 and the support section 50 to the outside by moving toward the proximal side (i.e., proximally relative to the incision section 40 and the support section 50).

The material of the outer sheath 80 is not particularly limited. For example, it is possible to favorably use polyolefin such as polyethylene, polypropylene, and the like; polyamide; polyester such as polyethylene terephthalate and the like; a fluorine-based polymer such as ETFE and the like; PEEK (polyether ether ketone); polyimide; and the like. In addition, the outer sheath 80 material may be configured to be made from a plurality of materials. A reinforcement member such as a wire material and the like may be embedded in the outer sheath 80.

The inner diameter of the outer sheath 80 can be suitably selected. For example, the inner diameter of the outer sheath 80 may range from 1.2 mm to 1.9 mm. As an example, the inner diameter of the outer sheath 80 can be set to 1.8 mm. The outer diameter of the outer sheath 80 can be suitably selected. For example, the outer diameter of the outer sheath 80 may range from 1.3 mm to 2.0 mm. As an example, the outer diameter of the outer sheath 80 can be set to 2.0 mm.

The inner tube 100 is disposed inside the linear motion shaft 70. The inner tube 100 is a pipe body (i.e., is tubular) having a lumen 101 through which the filter device 30, a guide wire, and the like can be inserted. The inner tube 100 is movable relative to the linear motion shaft 70 in the direction along the rotary axis "X" (i.e., the inner tube 100 is movable distally and proximally in the axial direction). At least a portion of the inner tube 100 possesses a plurality of hole portions 102 through which a fluid can circulate. The hole portions 102 penetrate the inner tube 100 from the inner peripheral surface to the outer peripheral surface (i.e., are through-holes or thru-holes). Similar to the hole portions 61 of the drive shaft 60, the hole portions 102 of the inner tube 100 may be a plurality of penetration holes which are provided in the pipe body. Alternatively, the hole portions 71 may be gaps in a braided body or a coil.

The material of the inner tube 100 is not particularly limited. For example, it is possible to favorably use polyolefin such as polyethylene, polypropylene, and the like; polyamide; polyester such as polyethylene terephthalate and the like; a fluorine-based polymer such as ETFE and the like; PEEK (polyether ether ketone); polyimide; and the like. In addition, the material of the inner tube 100 may be made from a plurality of materials. A reinforcement member such as a wire material and the like may be embedded in the inner tube 100.

The tip tube 90 is fixed to the distal side of linear motion shaft 70. The inner tube 100 is disposed inside the tip tube 90. A plurality of protrusion portions 91 are formed on the outer peripheral surface of the tip tube 90. For example, the protrusion portions 91 can be formed by performing embossing processing, can be formed by providing a plurality of holes, or can be formed by causing fine metal powder and the like to adhere on the front surface of the tip tube 90 or mixing fine metal powder and the like with the material of the tip tube 90. As the material of the metal powder, for example, stainless steel or the like can be favorably used.

The material of the tip tube 90 is not particularly limited. For example, polyolefin such as polyethylene, polypropylene, an ethylene-propylene copolymer, an ethylene-vinyl acetate copolymer, and the like; polyvinyl chloride; polystyrene; polyamide; polyimide; a combination thereof; or the like can be favorably used.

As illustrated in FIG. 1, the push-pull resistance measurement unit 130 (detection unit) includes a sensor 131 and a measurement device 132. The sensor 131 is configured to detect push-pull resistance (resistance in the axial direction) acting on the drive shaft 60 when pushing the incision section 40 and the support section 50 into a stenosed site and pulling the incision section 40 and the support section 50 back from the stenosed site. The measurement device 132 is configured to receive a signal from the sensor 131 and calculate the push-pull resistance. For example, the sensor 131 may be a strain gauge which is attached to a portion in the vicinity of a first bearing portion 171 receiving the push-pull resistance. The measurement device 132 calculates the push-pull resistance based on the signal received from the sensor 131 and transmits a result to the control unit 120. Note that the attachment portion of the sensor 131 is not particularly limited as long as the sensor 131 can detect push-pull resistance of the drive shaft 60.

As illustrated in FIGS. 1 and 5, the operation unit 110 includes a drive mechanism unit 170 which applies rotary force to the drive shaft 60, the movement mechanism unit 160 which moves the linear motion shaft 70 along the rotary axis "X" (i.e., moves the linear motion shaft 70 distally and proximally in the axial direction), and a liquid feeding unit 180 which feeds a physiological salt solution or the like (i.e., saline) into the outer sheath 80 (i.e., the liquid feeding unit 180 is configured to emit/transfer a physiological salt solution into the outer sheath 80).

The liquid feeding unit 180 includes a first housing 181. The outer sheath 80 is fitted in the first housing 181. The liquid feeding unit 180 also includes an accommodation bag 182 which accommodates (i.e., holds or contains) the physiological salt solution, a pressurization bag 183 which pressurizes the accommodation bag 182, a connection tube 184 which connects the accommodation bag 182 and the first housing 181, the first seal portion 185 which is disposed inside the first housing 181, and a fixing portion 188 which fixes the first seal portion 185.

The first housing 181 is a tubular member. A protruding second induction portion 186 is formed on the outer peripheral surface of the first housing 181. The protruding second induction portion 186 is slidably fitted in a straight second induction groove 175 formed on the outer peripheral surface of a second housing 173 which accommodates/contains a motor 178. The first housing 181 is movable with respect to the second housing 173 along the axial direction. The outer sheath 80 is fixed to the first housing 181 by being fitted from the distal side. For example, the first seal portion 185 is an O-ring or an X-ring, is disposed inside the proximal portion of the first housing 181, and slidably comes into contact with the coating portion 62 on the outer peripheral surface of the drive shaft 60 which passes through the inside of the outer sheath 80 and enters the inside of the first housing 181. The first seal portion 185 is fixed by the fixing portion 188 which is screwed into a threaded portion of the first housing 181 from the proximal side. The first seal portion 185 tolerates rotations and movement of the drive shaft 60 in the axial direction and maintains the liquid-tight state between the drive shaft 60 and the first housing 181.

The connection tube 184 extending from the accommodation bag 182 is connected/fitted to a port portion 187 which is formed in the first housing 181. The physiological salt solution supplied from the accommodation bag 182 can flow into the first housing 181 through the port portion 187. In the pressurized physiological salt solution flowing into the first housing 181, flow toward the proximal side is restricted by the first seal portion 185. The pressurized physiological salt solution can flow into the outer sheath 80 on the distal side. Note that, in the present embodiment, the liquid feeding unit 180 is slidably interlocked with the second housing 173. However, the liquid feeding unit 180 may have an independent configuration without being interlocked with the second housing 173. In this manner, the liquid feeding unit 180 can move in a wide range without being limited by the size of the second housing 173.

The drive mechanism unit 170 includes a drive gear 179 which meshes with the driven gear 64, the motor 178 which is a drive source including a rotary axis 178A to which the drive gear 179 is fixed, the control unit 120 which is configured to control the supply of a current to the motor 178, and the first bearing portion 171 and a second bearing portion 172 which rotatably support the linear motion shaft 70. Moreover, the drive mechanism unit 170 includes the second housing 173 which accommodates the motor 178, and a frame body 174 which is interlocked with the second housing 173 and holds the first bearing portion 171 and the second bearing portion 172.

As described above, the second housing 173 is a box-like member accommodating (i.e., housing or containing) the motor 178. The second induction portion 186 of the first housing 181 is slidably fitted in the second induction groove 175 which is formed on the outer surface of the second housing 173.

The frame body 174 includes a first partition wall 176 and a second partition wall 177 which are parallel to each other. The second housing 173 is fixed to the first partition wall 176 on the distal side, and the movement mechanism unit 160 is fixed to the second partition wall 177 on the proximal side.

The rotary axis 178A extending from the motor 178 inside the second housing 173 penetrates the first partition wall 176. The drive gear 179 is disposed between the first partition wall 176 and the second partition wall 177. In addition, the first bearing portion 171 is disposed in the first partition wall 176, and the drive shaft 60 extending from the first housing 181 is rotatably held by the first bearing portion 171. The driven gear 64 fixed to the drive shaft 60 is positioned between the first partition wall 176 and the second partition wall 177 and meshes with the drive gear 179. The second bearing portion 172 which rotatably supports the drive shaft 60 is disposed in the second partition wall 177.

When electricity is supplied to the motor 178 via a cable 121, and the rotary axis 178A of the motor 178 is rotated, the driven gear 64 meshing with the drive gear 179 rotates. The driven gear 64 thus rotates the drive shaft 60 supported by the first bearing portion 171 and the second bearing portion 172. When the drive shaft 60 rotates, the incision section 40, the support section 50, and the tip tube 90 which are fixed to the drive shaft 60 on the distal side rotate. Since the distal side end portion 54 of the support section 50 is bonded to the linear motion shaft 70, when the support section 50 rotates, the linear motion shaft 70 also rotates following the support section 50.

Figure 10:
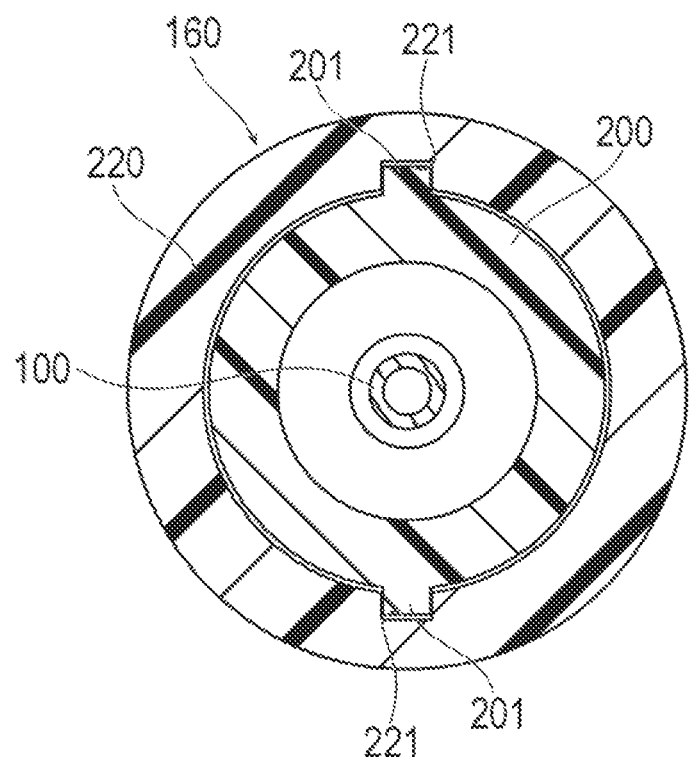
FIG. 10 is a cross-sectional view taken along line E-E in FIG. 5.

As illustrated in FIGS. 1, 5 and 10, the movement mechanism unit 160 includes a dial 190 which an operator can rotate by using their fingers, a movement base 200 which can linearly move (i.e., in the axial direction) in accordance with the rotations of the dial 190, a third bearing portion 161 which is fixed to the movement base 200 and rotatably holds the linear motion shaft 70, a second seal portion 162, and a proximal fixing portion 210 which fixes the second seal portion 162 (i.e., the proximal fixing portion 210 holds the second seal portion 162 in place). Moreover, the movement mechanism unit 160 includes a third housing 220 which accommodates the movement base 200. A protruding first induction portion 201 formed in the movement base 200 is slidably fitted in a straight first induction groove 221 which is formed on the inner surface of the third housing 220.

The dial 190 is a cylindrical member which is disposed on the proximal side of the frame body 174. The dial 190 can be rotated when the outer peripheral surface of the dial 190 is operated (i.e., by a user's fingers). A portion of the distal portion of the dial 190 is positioned inside the third housing 220. A groove portion 192 extending in the circumferential direction on the outer peripheral surface is formed in the dial 190. A hook portion 222 formed in the proximal portion of the third housing 220 is fitted in the dial 190 so that movement by the dial 190 in the axial direction is regulated, and the dial 190 is rotatably held with respect to (i.e., relative to) the third housing 220. A feed screw 191 screwed to a screw groove 202 (which is formed in the movement base 200) is formed on the inner peripheral surface of the dial 190. The dial 190 includes a discharge hole 196 through which the air inside the dial 190 is released during priming. The discharge hole 196 can be opened and closed by a plug 197.

The first induction portion 201 and the screw groove 202 are formed in the movement base 200. The first induction portion 201 is fitted in the first induction groove 221 of the third housing 220, and the feed screw 191 is screwed onto the screw groove 202 (i.e., the feed screw 191 and the screw groove 202 may be threaded/unthreaded from one another). Therefore, when the feed screw 191 rotates, the movement base 200 can move non-rotatively with respect to the third housing 220 to move linearly along the rotary axis "X" (i.e., in the axial direction). Since the third bearing portion 161 fixed to the movement base 200 causes a movement force to act on the linear motion shaft 70 in accordance with movement of the movement base 200, it is preferable that the third bearing portion 161 is a bearing which can receive force in the axial direction (thrust force). A different seal member may be provided on the proximal side of the third bearing portion 161.

The second seal portion 162 can be accommodated inside a recessed portion 194 on the proximal side of the dial 190. The second seal portion 162 surrounds a penetration hole 193 which the linear motion shaft 70 of the dial 190 penetrates. The second seal portion 162 is an annular member. The inside of the second seal portion 162 comes into contact with the outer peripheral surface of the proximal portion of the linear motion shaft 70.

The proximal fixing portion 210 is a screwable bolt-like member which is screwed into a screw groove 195 formed in the recessed portion 194 of the dial 190 (i.e., the proximal fixing portion 210 is threadedly engaged with the screw groove 195). The inner tube 100 is disposed in a penetration hole 211 formed inside the proximal fixing portion 210. When being screwed into the recessed portion 194 of the dial 190, the proximal fixing portion 210 causes the second seal portion 162 to deform, presses the inner tube 100, and holds the inner tube 100 while maintaining the liquid-tight state between the dial 190 and the inner tube 100.

The control unit 120 is configured to supply a current to the motor 178 via the cable 121 and also functions as a detection unit to detect a change in the supplying current. The control unit 120 can detect the incision resistance (i.e., the resistance in the rotation direction) in the incision section 40 which is rotationally driven by the motor 178. In addition, the control unit 120 receives a measurement result of the push-pull resistance (i.e., the resistance in the axial direction) acting on the drive shaft 60 from the measurement device 132. In a case where the incision resistance exceeds the threshold value set in advance, the control unit 120 stops the motor 178 from rotating and causes the notification unit 150 to display the fact that the incision resistance exceeds the threshold value. The control unit 120 may instead be configured to lower the rotational frequency instead of stopping the motor 178 from rotating when the incision resistance exceeds the threshold value. When the push-pull resistance exceeds the threshold value set in advance, the control unit 120 is further configured to stop the motor 178 from rotating and cause the notification unit 150 to display the fact that the push-pull resistance exceeds the threshold value. The control unit 120 may instead be configured to lower the rotational frequency instead of stopping the motor 178 from rotating when the push-pull resistance exceeds the threshold value.

The notification unit 150 includes a monitor 151 and a speaker 152 which are connected to and can communicate with the control unit 120. The monitor 151 displays the fact that the incision resistance and/or the push-pull resistance exceeds the threshold value, thereby notifying an operator of the medical device 10. The speaker 152 notifies the operator that the incision resistance or the push-pull resistance exceeds the threshold value by emitting a sound. When the incision resistance or the push-pull resistance exceeds the threshold value, the control unit 120 may be configured to only issue notification through the notification unit 150 without stopping the motor 178 from rotating. In this case, the operator can visually or acoustically receive the notification from the notification unit 150, and then decide to stop the motor 178, to stop pushing-in or pulling-back, or to change the diameter of the incision section 40 by rotating the dial 190.

Figure 12:
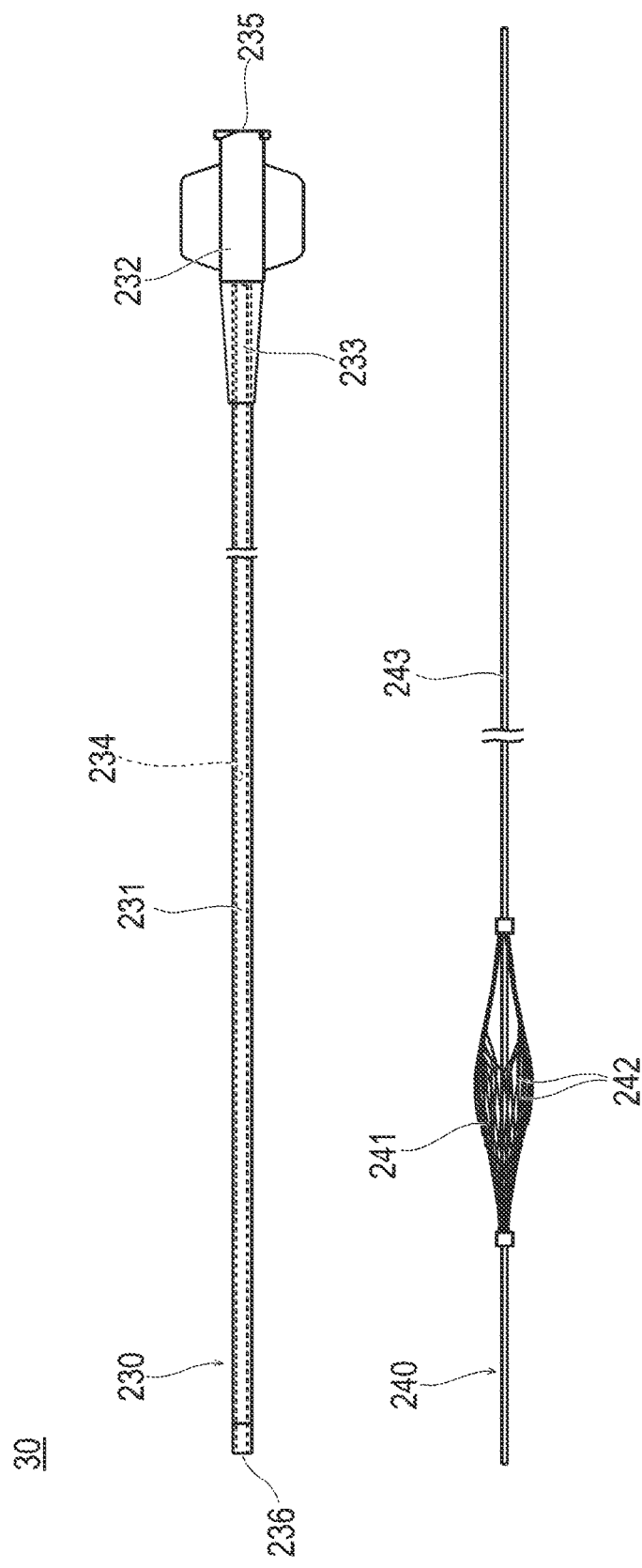
FIG. 12 is a plan view illustrating a filter device.

As illustrated in FIGS. 1 and 12, the filter device 30 includes a filter instrument 240 which functions as a filter, and a sheath 230 which can store the filter instrument 240.

The filter instrument 240 includes a filter portion 241 which is braided by using a plurality of wires 242, and a long shaft portion 243 which penetrates the filter portion 241 and is interlocked with the filter portion 241.

The filter portion 241 is contractible when being accommodated inside the sheath 230 and is expandable due to the self-expanding force when being released from the sheath 230 (i.e., the filter portion 241 is self-expanding). In the filter portion 241, the distal side is interlocked with (i.e., connected to) a shaft portion 243 in a closed cage shape, and the proximal side on which the plurality of wires 242 are twisted and gathered is interlocked with (i.e., connected to) the shaft portion 243.

The outer diameter of each wire 242 can be suitably selected depending on the material, the usage, or the like of the wire 242. For example, the outer diameter of each wire 242 may range from 20 µm to 100 µm. As an example, the outer diameter of each wire 242 can be set to 40 µm.

It is preferable that each of the wires 242 is a flexible material. For example, it is possible to favorably use a shape memory alloy in which a shape memory effect and superelasticity are applied through heat treatment; stainless steel; Ta; Ti; Pt; Au; W; polyolefin such as polyethylene, polypropylene, and the like; polyamide; polyester such as polyethylene terephthalate and the like; a fluorine-based polymer such as ETFE and the like; PEEK (polyether ether ketone); polyimide; and the like. As the shape memory alloy, a Ni—Ti-based alloy, a Cu—Al—Ni-based alloy, a Cu—Zn—Al-based alloy, a combination of these alloys, or the like is preferably used. As a structure in which a plurality of materials are combined together, for example, it is possible to exemplify a structure in which a core wire made from Pt is coated with a Ni—Ti alloy in order to apply contrast properties, and a structure in which a core wire made from a Ni—Ti alloy is subjected to gold plating.

The material of the shaft portion 243 is not particularly limited. For example, stainless steel, a shape memory alloy, or the like can be favorably used.

The sheath 230 includes a pipe body 231, a hub 232, and an anti-kink protector 233. The pipe body 231 includes a lumen 234 which can accommodate the filter instrument 240. The pipe body 231 is open (i.e., is a hollow cylindrical tube). The pipe body 231 opens at a pipe body opening portion 236 which is formed in the distal side end portion. The hub 232 is fixed to the proximal side end portion of the pipe body 231. The hub 232 includes a hub opening portion 235 which communicates with the lumen 234. The anti-kink protector 233 is a soft member (i.e., relatively soft) which covers an interlock portion of the pipe body 231 and the hub 232. The kink-resistant protector 233 prevents a kink of the pipe body 231.

The material of the pipe body 231 is not particularly limited. For example, the pipe body 231 may be polyolefin such as polyethylene, polypropylene, an ethylene-propylene copolymer, an ethylene-vinyl acetate copolymer, and the like; polyvinyl chloride; polystyrene; polyamide; polyimide; a combination of these materials; or the like.

A method of using the medical device 10 of the present embodiment will be described with reference to an example of a case where a stenotic substance inside a blood vessel is incised by the medical device 10.

Figure 13A:
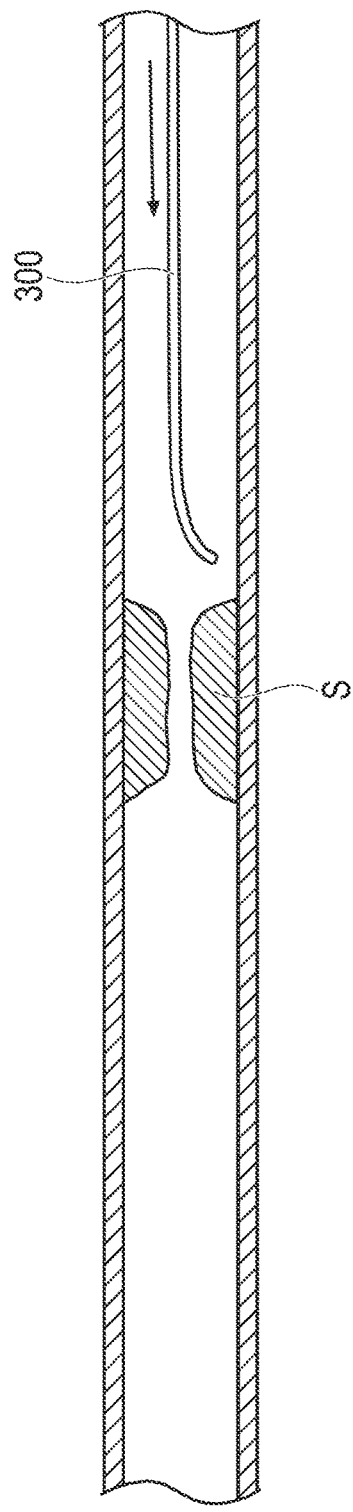
FIGS. 13A and 13B are schematic sectional views illustrating a state inside a blood vessel when the procedure is performed.
Figure 13B:
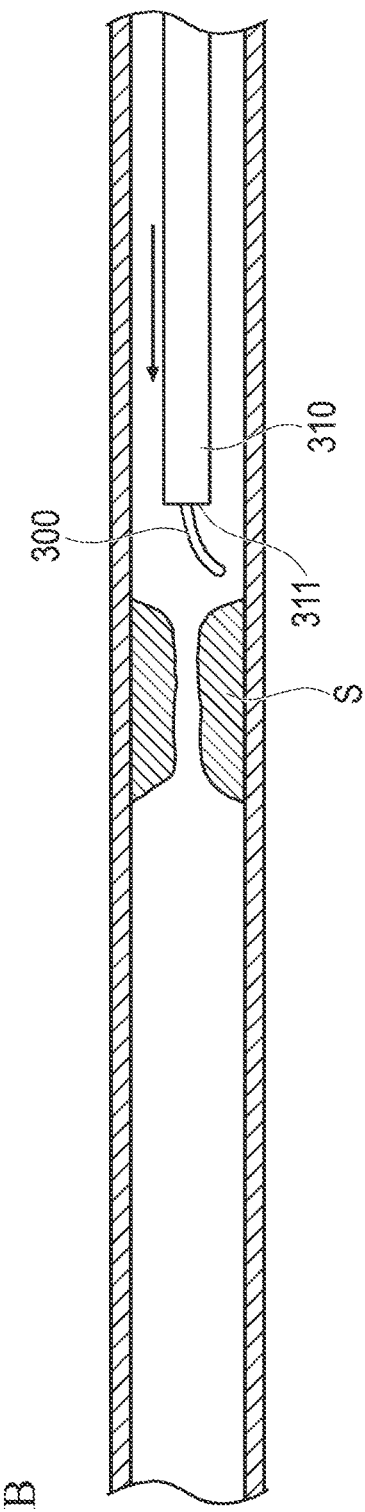

First, an introducer sheath (not illustrated) is inserted into a blood vessel on an upstream side (proximal side) from a stenosed site S in the blood vessel in a transcutaneous manner. A guide wire 300 is inserted into the blood vessel via the introducer sheath. Subsequently, the guide wire 300 is pushed ahead to reach the proximal side from the stenosed site S as illustrated in FIG. 13A. The proximal side end portion of the guide wire 300 positioned outside a human body is inserted into a catheter opening portion 311 of a guiding catheter 310 on the distal side. The guiding catheter 310 is inserted into the blood vessel along the guide wire 300 as illustrated in FIG. 13B to reach the proximal side from the stenosed site S.

Subsequently, the proximal side end portion of the guide wire 300 positioned outside the human body is inserted into a catheter opening portion 321 of a support catheter 320 on the distal side. After the support catheter 320 is pushed ahead to the proximal side from the stenosed site S (i.e., moves proximally) as illustrated in FIG. 14A, the support catheter 320 and the guide wire 300 reach the distal side from the stenosed site S. Thereafter, the guide wire 300 is removed, with the support catheter 320 remaining inside the blood vessel.

Subsequently, the filter device 30 having the filter instrument 240 accommodated inside the sheath 230 is prepared. The filter portion 241 is positioned close to the distal side end portion of the pipe body 231 of the sheath 230, and the shape of the filter portion 241 is restrained in the contraction state (i.e., the sheath 230 holds the filter portion 241 in the contracted state within the sheath 230). As illustrated in FIG. 14B, the filter device 30 is then inserted into the blood vessel via the support catheter 320 on the distal side from the stenosed site S (i.e., distally of the stenosed site S). Thereafter, the support catheter 320 is retracted (i.e., moved proximally).

The sheath 230 is moved proximally relative to the filter instrument 240, causing the filter portion 241 to protrude from the pipe body 231 on the distal side (i.e., the distal-most end of the filter portion 241 is moved to be distal of the distal-most end of the pipe body 231). Accordingly, as illustrated in FIG. 15A, the filter portion 241 expands into the expansion state due to the self-restoring force (i.e., the filter portion 241 self-expands). The outer circumferential portion of the cage-shaped filter portion 241 comes into contact with an inner wall surface of the blood vessel. In this case, the filter portion 241 is open toward the stenosed site S on the upstream side (proximal side). As illustrated in FIG. 15B, the sheath 230 is then retracted while the filter instrument 240 is retained in place.

Figure 16:
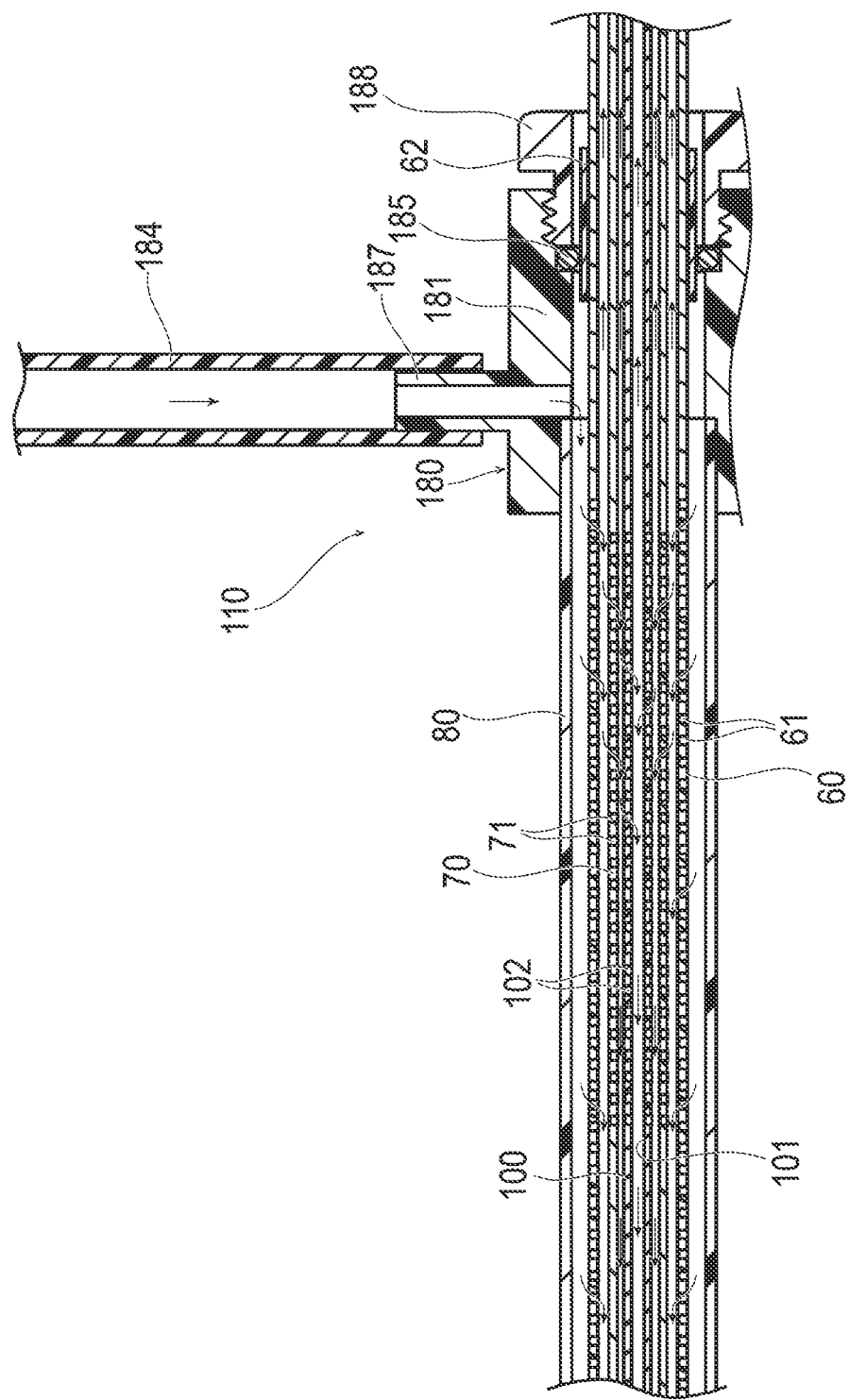
FIG. 16 is a longitudinal sectional view illustrating the proximal portion of the treatment device when a physiological salt solution is supplied from a liquid feeding unit.

The treatment device 20 is prepared by causing the incision section 40 and the support section 50 to contract and to be accommodated inside the outer sheath 80. The accommodation bag 182 is pressurized by the pressurization bag 183, and the physiological salt solution is supplied to the inside of the first housing 181 from the accommodation bag 182 via the connection tube 184. As illustrated in FIG. 16, in the physiological salt solution flowing into the first housing 181, the proximal movement of the physiological salt solution is regulated by the first seal portion 185 (i.e., the first seal portion 185 prevents the physiological salt solution from flowing proximally beyond the first seal portion 185). The physiological salt solution passes through the inside of the outer sheath 80 and moves in the direction toward the distal side (i.e., moves distally). When the physiological salt solution flowing into the outer sheath 80 reaches a the hole portions 61 of the drive shaft 60, a portion of the physiological salt solution passes through the hole portions 61 and flows into the drive shaft 60. When the physiological salt solution flowing into the drive shaft 60 reaches the hole portions 71 of the linear motion shaft 70, a portion of the physiological salt solution passes through the hole portions 71 and flows into the linear motion shaft 70 (i.e., at least a portion of the physiological salt solution that passes through the hole portions 61 of the drive shaft also passes through the hole portions 17 of the linear motion shaft 70). When the physiological salt solution flowing into the linear motion shaft 70 reaches the hole portions 102 of the inner tube 100, a portion of the physiological salt solution passes through the hole portions 102 and flows into the lumen 101 of the inner tube 100.

Figure 17:
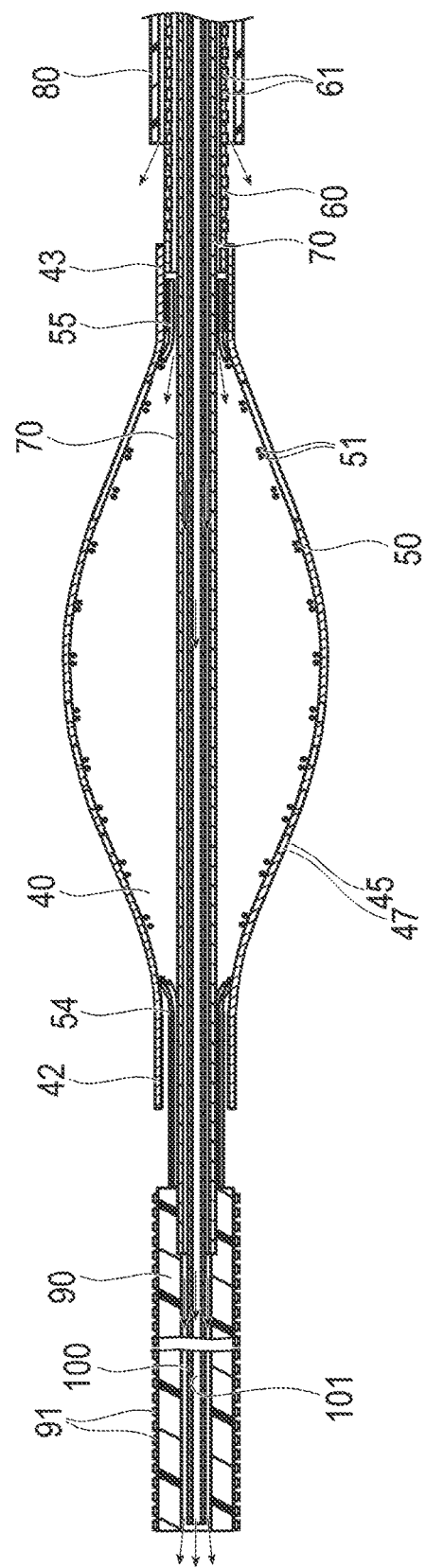
FIG. 17 is a longitudinal sectional view illustrating the distal portion of the treatment device when priming is performed.
Figure 18:
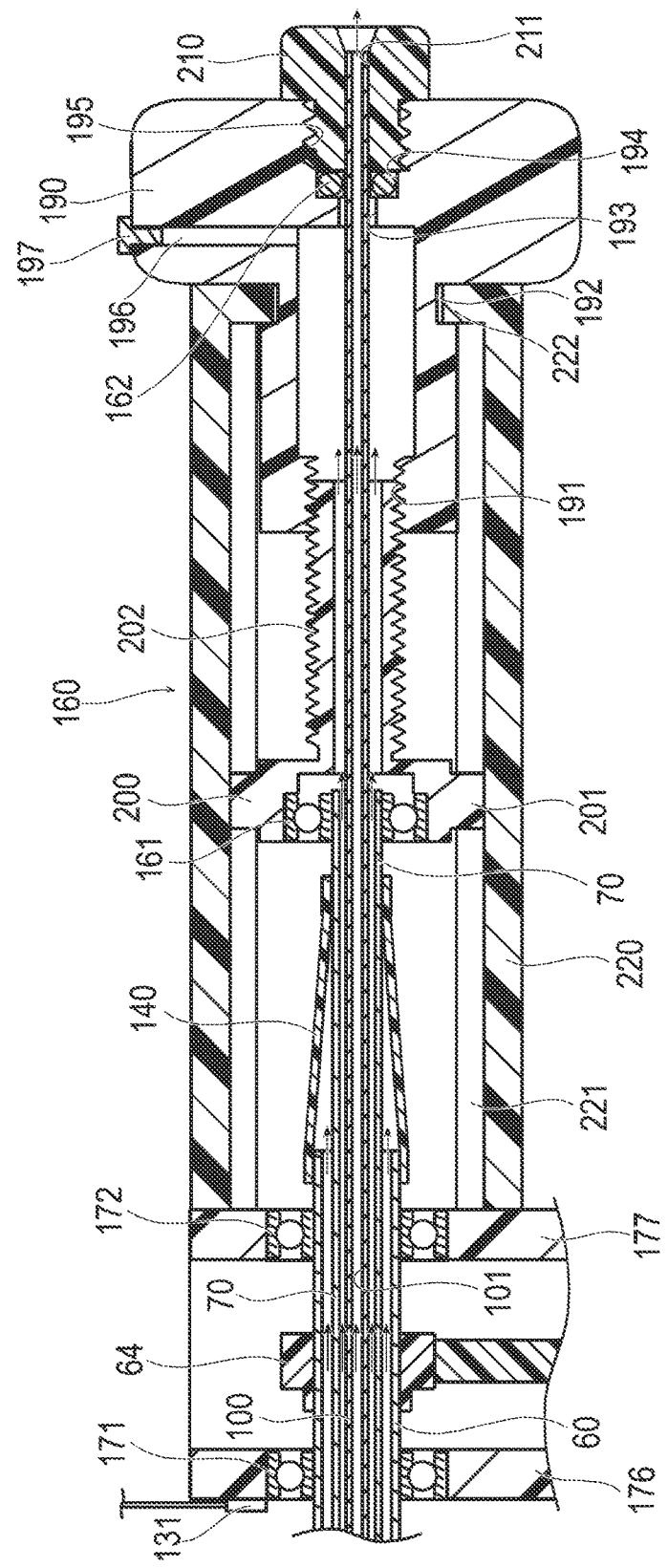
FIG. 18 is a longitudinal sectional view illustrating the proximal portion of the treatment device when priming is performed.

As illustrated in FIG. 17, the physiological salt solution flowing into the outer sheath 80, the drive shaft 60, the linear motion shaft 70, and the inner tube 100 is released through the opening portion on the distal side of the outer sheath 80, the drive shaft 60, the linear motion shaft 70, and the inner tube 100. In the physiological salt solution flowing proximally into the drive shaft 60 as illustrated in FIG. 18, the physiological salt solution movement is regulated by the interlock portion 140 which is interlocked with (i.e., connected to) the proximal portion of the drive shaft 60 and the linear motion shaft 70. The physiological salt solution flowing into the linear motion shaft 70 flows in the direction toward the proximal side (i.e., proximally), passes through the inside of the movement base 200, and flows into the dial 190. The physiological salt solution flowing into the dial 190 passes through the discharge hole 196 and is discharged to the outside. After the air inside the movement base 200 and the dial 190 is released, the discharge hole 196 can be blocked by a plug 197. The physiological salt solution flowing into the inner tube 100 flows in the direction toward the proximal side (i.e., proximally) and is discharged to the outside through the opening portion 211 on the proximal side. Priming is completed in this manner. Note that, liquid-feeding from the accommodation bag 182 continues thereafter until the procedure using the treatment device 20 is completed. In addition, priming of the treatment device 20 may be performed without adopting the pressurization bag 183.

The amount of the physiological salt solution flowing into the proximal side may additionally be regulated by decreasing the diameter of the proximal portion of the linear motion shaft 70 and sufficiently reducing the clearance with respect to the inner tube 100. Accordingly, it is possible to prevent the physiological salt solution from leaking through the gap between the feed screw 191 and the screw groove 202, and the third bearing portion 161. Note that, in order to prevent the physiological salt solution from leaking through the third bearing portion 161, it is possible to utilize a sealed bearing.

Subsequently, the proximal side end portion of the shaft portion 243 is inserted into the distal side opening portion of the inner tube 100, and as illustrated in FIG. 19A, the distal portion of the treatment device 20 is moved to the inside of the blood vessel via the guiding catheter 310. The distal portion of the treatment device 20 is positioned on the proximal side from the stenosed site S under radioscopy (i.e., while the operator views the procedure using radioscopy). The accommodation bag 182 supplies the physiological salt solution to the treatment device 20 at all times. Therefore, blood is prevented from flowing into the outer sheath 80, the drive shaft 60, the linear motion shaft 70, and the inner tube 100.

Figure 20:
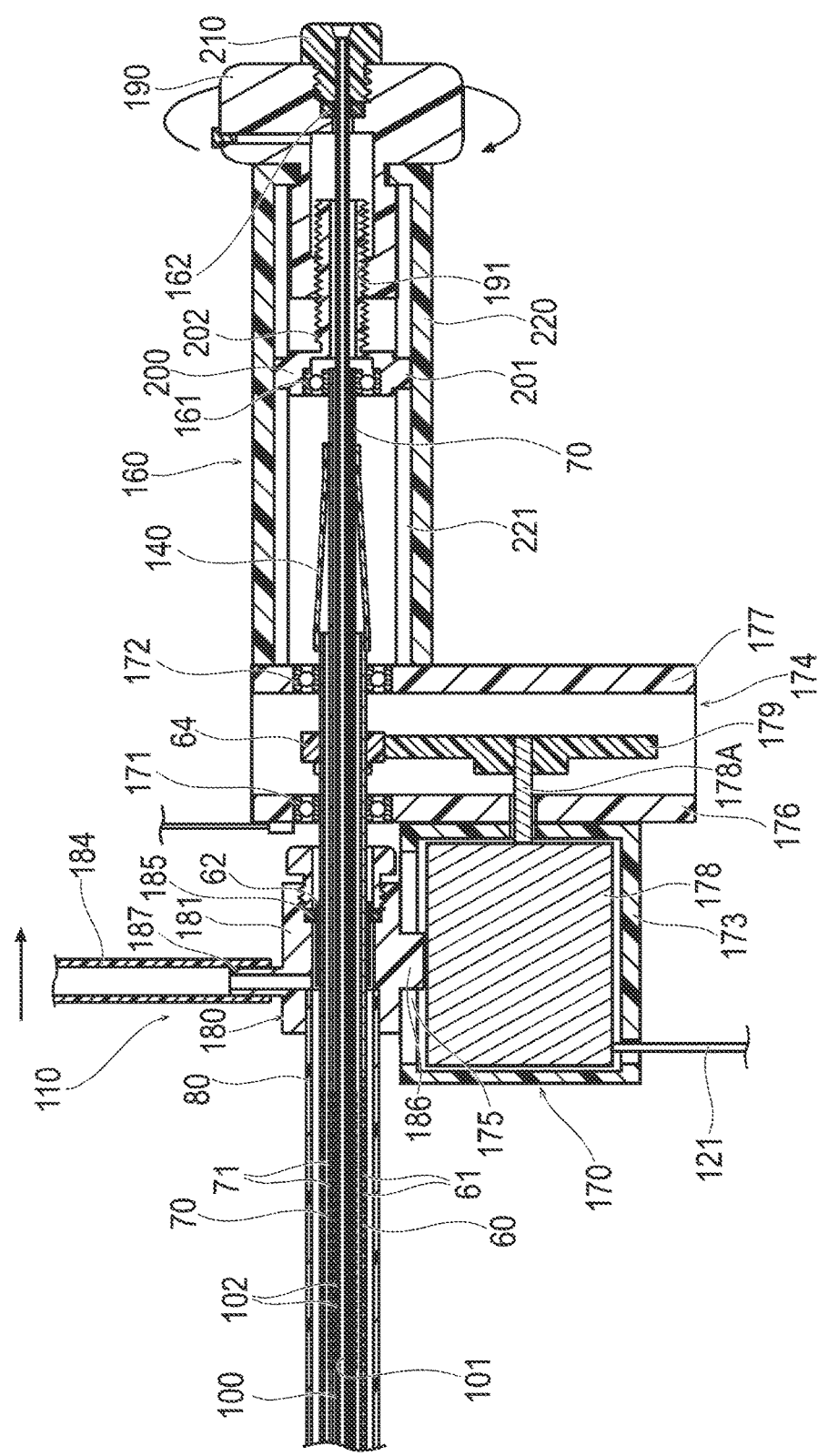
FIG. 20 is a longitudinal sectional view illustrating the proximal portion when a dial of the treatment device is rotated.

When the first housing 181 is moved toward the proximal side with respect to the second housing 173 as illustrated in FIG. 20, the outer sheath 80 moves toward the proximal side as illustrated in FIG. 19B. This proximal movement/retraction of the outer sheath 80 exposes the incision section 40 and the support section 50 inside the blood vessel. When the outer sheath 80 exposes the incision section 40 and the support section 50, the incision section 40 and the support section 50 are in the contracted state on the proximal side from the stenosed site S (i.e., the incision section 40 and the support section 50 do not expand radially outward and remain contracted).

The size of the gap at/through the stenosed site S is detected under radioscopy. The size of the gap at/through the stenosed site S can be visually detected from an X-rayed image, or the size of the gap at/through the stenosed site can be detected, for example, by comparing the gap at the stenosed site S in the X-rayed image with a portion of the treatment device 20 of which the dimensions are known (for example, the struts 41 or the support section 50). In addition, the size of the gap at/through the stenosed site S can be more minutely (precisely) detected by utilizing an intra vascular ultrasound (IVUS) apparatus, an optical coherence tomography (OCT) apparatus, or an optical frequency domain imaging (OFDI) method.

Thereafter, as illustrated in FIG. 20, the dial 190 is rotated to rotate the feed screw 191 and to move the movement base 200 toward the proximal side (i.e., proximally). Then, the linear motion shaft 70 interlocked with the movement base 200 moves toward the proximal side (i.e., proximally in the axial direction) with respect to (i.e., relative to) the drive shaft 60. When the linear motion shaft 70 moves toward the proximal side, the distal side end portion 54 and the proximal side end portion 55 become closer to each other (i.e., the distal end portion 54 moves proximally relative to the proximal side end portion 55 to close the gap/space between the portions). As illustrated in FIGS. 11A, 11B, and 21A, the intermediate portion of the support section 50 is deformed to be flexed radially outward, thereby being in the expansion state. When the intermediate portion of the support section 50 is flexed radially outward, the struts 41 disposed on the outer side of the support section 50 are pressed radially outward by the support section 50, thereby expanding. Since the distal end portion 42 of the incision section 40 is not fixed to the support section 50 and the linear motion shaft 70 (at least in the initial stage of expansion), force in the axial direction does not act between the distal end portion 42 and the proximal fixing end 43. Accordingly, as illustrated in FIG. 11A, the incision section 40 expands only by the radially outward force received from the support section 50. Therefore, gaps are unlikely to be generated among (i.e., between) the struts 41 and the wire materials 51. When the linear motion shaft 70 moves toward the proximal side with respect to (i.e., moves proximally relative to) the drive shaft 60, the interlock portion 140 interlocking the proximal portion of the linear motion shaft 70 and the proximal portion of the drive shaft 60 with each other is stretched as illustrated in FIG. 20. Thus, the liquid-tight state is maintained. The physiological salt solution flowing into the space between the linear motion shaft 70 and the drive shaft 60 does not leak (i.e., flow proximally beyond the interlock portion 140).

The sizes of the incision section 40 and the support section 50 can be arbitrarily adjusted in accordance with the rotation quantity of the dial 190. Therefore, the size of the incision section 40 at the time of expansion can be arbitrarily adjusted (i.e., an operator can control the size adjustments) to a desirable size, and thus, effective incision can be performed.

When the support section 50 and the incision section 40 are caused to expand by rotating the dial 190, the expansion diameter of the incision section 40 is compared with the gap at the stenosed site S under radioscopy. The support section 50 and the incision section 40 are expanded to be greater than the gap at the stenosed site S. The outer diameters of portions at which the incision section 40 and the support section 50 maximally expand (i.e., the maximum outer diameter of the incision section 40 and the support section 50) range from: i) the diameters in the minimum contraction state where the incision section 40 and the support section 50 minimally contract; to ii) the diameters in the maximum expansion state where the incision section 40 and the support section 50 maximally expand.

When a current is supplied to the motor 178 by the control unit 120 to rotate the motor 178, the drive force of the motor 178 is transmitted from the drive gear 179 to the driven gear 64. The drive shaft 60 interlocked with the driven gear 64 thus rotates, and the incision section 40 and the support section 50 interlocked with the drive shaft 60 rotate. When the incision section 40 and the support section 50 rotate, the linear motion shaft 70 interlocked with the support section 50 on the distal side also rotates. In addition, since the linear motion shaft 70 is interlocked with the drive shaft 60 on the proximal side by the interlock portion 140, the linear motion shaft 70 also receives rotary force from the proximal side. Therefore, the linear motion shaft 70 is likely to rotate while following the drive shaft 60 without delay (i.e., the linear motor shaft 70 rotates with the drive shaft 60). Thus, torsion of the linear motion shaft 70 can be prevented. When torsion of the linear motion shaft 70 can be prevented, the work for distorting the linear motion shaft 70 is no longer necessary, and the drive force can be effectively transmitted. Thus, the medical device 10 can be driven at low torque. In addition, since the interlock portion 140 is positioned outside the human body during the procedure, safety can be ensured even if the interlock portion 140 breaks.

The drive shaft 60 can smoothly rotate because the drive shaft 60 is rotatably supported by the first bearing portion 171 and the second bearing portion 172. Inside the first housing 181, the first seal portion 185 comes into contact with the coating portion 62 provided on the outer peripheral surface of the drive shaft 60, and the coating portion 62 slides with respect to (i.e., relative to) the first seal portion 185 when the drive shaft 60 rotates. However, since the coating portion 62 is formed from a low-friction material, rotations of the drive shaft 60 are seldom hindered (i.e., the first seal portion 185 does not impart a friction force on the drive shaft 60). The linear motion shaft 70 can smoothly rotate because the proximal portion is rotatably supported by the third bearing portion 161.

As illustrated in FIG. 21B, the treatment device 20 is pushed ahead (i.e., moves distally) when the incision section 40 and the support section 50 rotate. Accordingly, the blade 47 formed in the incision section 40 and the protrusion portions 91 formed in the tip tube 90 (refer to FIG. 17) come into contact with the stenosed site S. The stenotic substance is scraped off and becomes debris D, thereby flowing toward the distal side (downstream side). The debris D flowing toward the distal side enters the inside of the filter portion 241 positioned on the distal side, and the debris D is captured by the filter portion 241 so as to be filtered. Accordingly, the debris D can be prevented from flowing toward peripheral blood vessels. Therefore, it is possible to prevent a new stenosed site occurring in peripheral blood vessels.

When the stenosed site S is incised, the support section 50 affecting biological tissue less than the struts 41 (i.e., damaging the biological tissue less than the struts 41) comes into contact with the biological tissue because the support section 50 protrudes radially outward from between the struts 41. The support section 50 thus protrudes radially outward from between the struts 41 so that damage to normal biological tissue can be prevented by the edge portions of the struts 41, and thus, safety can be enhanced.

In addition, since the distal end portion 42 of the incision section 40 is not fixed to the support section 50 and/or the linear motion shaft 70, and the incision section 40 expands by the radially outward force received from the support section 50 in the initial stage of expansion, gaps are unlikely to be generated among/between the struts 41 and the wire materials 51. Accordingly, the hard fallen debris D and/or the stenotic substance is unlikely to be interposed among/between the struts 41 and the wire materials 51. Therefore, the struts 41 are not contacted/deformed (i.e., the struts 41 remain in good shape/condition) by the hard fallen debris D. The struts 41 can thus be prevented from being damaged or ruptured, and normal biological tissue can be prevented from being damaged (i.e., unintended damage) by the edge portions of the struts 41.

After the incision section 40 is pushed ahead (i.e., moved distally) and the stenosed site S is incised and before the incision section 40 completely passes through the stenosed site S (i.e., moves beyond the distal end of the stenosed site S), the treatment device 20 can be pulled back (i.e., moved proximally/retracted). When pushing-in and pulling-back of the treatment device 20 are repeated (i.e., performed consecutively), the incision section 40 can be gradually pushed ahead with respect to (i.e., moved distally relative to) the stenosed site S. The stenosed site S can thus be incised little by little (i.e., in a step-wise manner). Accordingly, surplus force can be prevented from acting on the incision section 40 (i.e., excess force on the incision section 40 can be avoided), and the incision section 40 can be prevented from being damaged or ruptured.

When surplus incision resistance (resistance in the rotation direction) acts on the incision section 40, a change occurs in a current driving the motor 178, and the control unit 120 detects the change in the current. The control unit 120 specifies (i.e., identifies) the incision resistance from the detected current. In a case where the incision resistance exceeds the threshold value set in advance, the control unit 120 stops the motor 178 from rotating. The control unit 120 causes the monitor 151 to display the fact that the incision resistance exceeds the threshold value and issues notification by a sound through the speaker 152.

In addition, when surplus push-pull resistance (i.e., excess resistance in the axial direction) acts on the incision section 40, the surplus push-pull resistance is detected by the push-pull resistance measurement unit 130, and a notification is issued to the control unit 120. In a case where the push-pull resistance exceeds the threshold value set in advance, the control unit 120 stops the motor 178 from rotating. The control unit 120 causes the monitor 151 to display the fact that the push-pull resistance exceeds the threshold value and issues notification by a sound through the speaker 152.

Figure 22A:
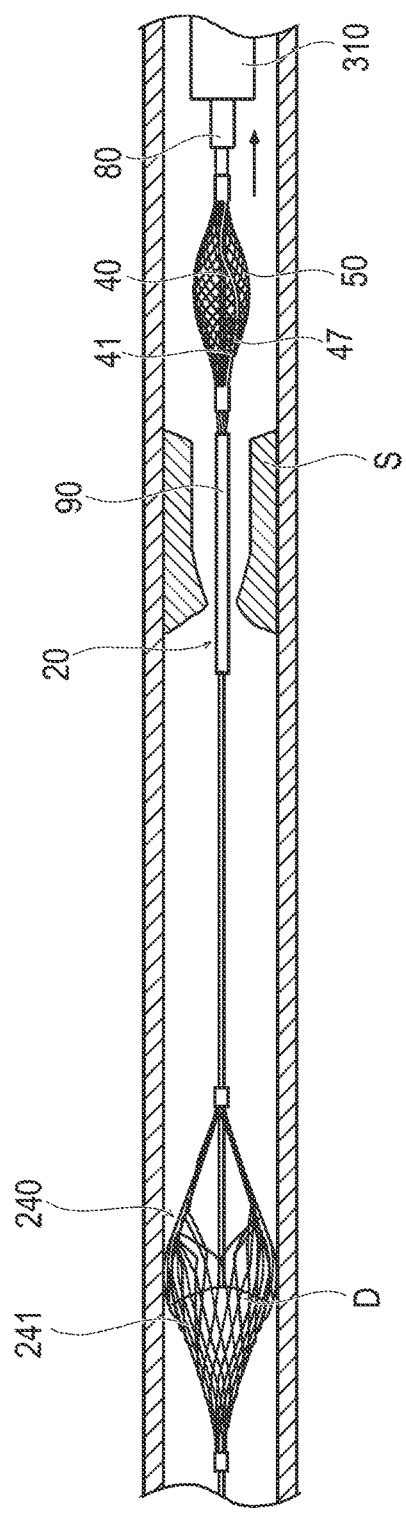
FIGS. 22A and 22B are schematic sectional views illustrating a state inside a blood vessel when the procedure is performed.

If the motor 178 is stopped when surplus incision resistance or surplus push-pull resistance generated in the incision section 40 is detected, incision performed by the incision section 40 can be discontinued before the incision section 40 is damaged or ruptured. After the motor 178 stops rotating, as illustrated in FIG. 22A, the treatment device 20 is pulled back and the motor 178 is rotated again by operating the control unit 120. It is thus possible to restart incision by using the treatment device 20. Note that, when the incision resistance or the push-pull resistance exceeds the threshold value, the control unit 120 may lower the rotational frequency instead of stopping the motor 178 from rotating. In addition, the control unit 120 may only urge a user to stop the motor 178, through the notification unit 150 (e.g., an audio or visual notification), without stopping the motor 178 from rotating.

Figure 22B:
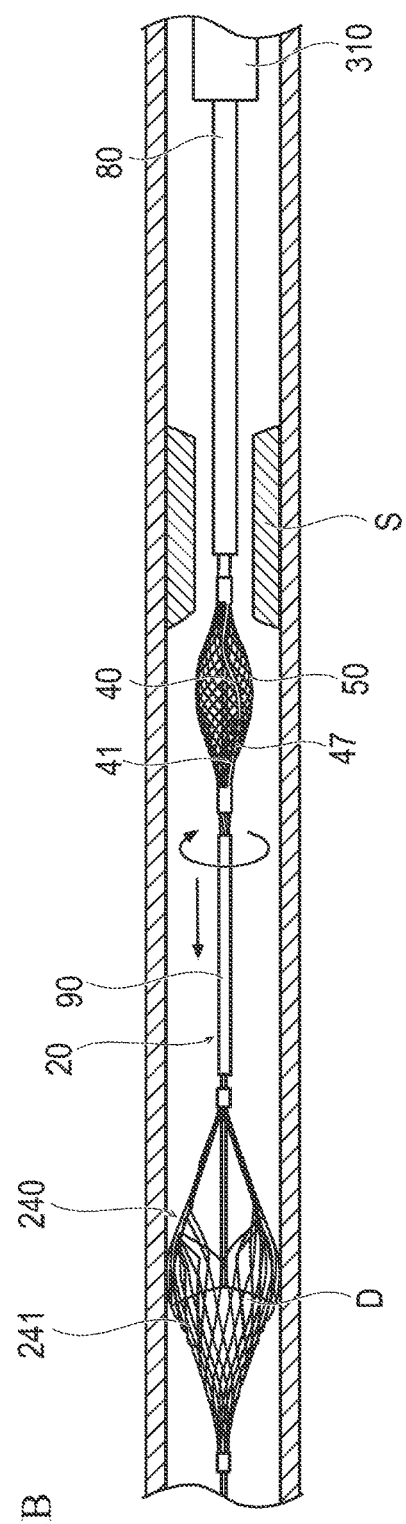

As illustrated in FIG. 22B, after the incision section 40 passes through the stenosed site S, the treatment device 20 is pulled back (i.e., moved proximally/retracted). The incision section 40 is then moved toward the proximal side from the stenosed site S (i.e., moves proximally) as illustrated in FIG. 23A, and the drive shaft 60 is stopped from rotating. Subsequently, the dial 190 is rotated again, and as illustrated in FIG. 23B, the incision section 40 is caused to further expand (i.e., to have a larger outer diameter than during the previous incision/cutting step). Similar to the above-described operation, the stenosed site S is incised little by little (i.e., in a step-wise manner) by repeatedly pushing-in and pulling-back (i.e., distally and proximally moving) of the treatment device 20 while rotating the incision section 40. FIGS. 24A and 24B illustrate this incremental incising process. As discussed above, the rotation of the incision section 40 is stopped through the control unit 120 when the incision resistance or the push-pull resistance exceeds the threshold value. After the incision section 40 passes through the stenosed site S, the treatment device 20 is pulled back (i.e., moved proximally or retracted), and the incision section 40 is moved toward the proximal side from the stenosed site S, thereby stopping the drive shaft 60 from rotating. While the incision section 40 is caused to gradually expand, pushing-in and pulling-back of the incision section 40 are repeated with respect to the stenosed site S, thereby incising the stenosed site S. In this manner, when the stenosed site S is incised by causing the incision section 40 to gradually expand, surplus (i.e., excessive) force can be prevented from acting on the incision section 40, and the incision section 40 can be prevented from being damaged or ruptured.

After incision of the stenosed site S performed by the incision section 40 is completed, the dial 190 is rotated in a direction opposite to the direction that the dial 190 is rotated to cause the incision section 40 and the support section 50 to expand. Accordingly, as illustrated in FIG. 5, the feed screw 191 rotates, the movement base 200 moves toward the distal side, and the linear motion shaft 70 interlocked with the movement base 200 moves toward the distal side. When the linear motion shaft 70 moves toward the distal side, as illustrated in FIG. 4, the distal side end portion 54 of the support section 50 moves to be separated from the proximal side end portion 55 (i.e., the distal side end portion 54 moves distally relative to the proximal side end portion 55 to increase the space/gap between the portions). This causes the incision section 40 and the support section 50 to be in a state of contracting radially inward (i.e., the incision section and the support section 50 thus contract radially inward). Subsequently, when the first housing 181 is moved toward the distal side with respect to the second housing 173, the outer sheath 80 moves toward the distal side. The incision section 40 and the support section 50 are thus accommodated inside the outer sheath 80 as illustrated in FIG. 25A. Thereafter, the treatment device 20 is retracted to the outside of the human body (i.e., removed from the living body) via the guiding catheter 310.

The sheath 230 is then inserted into the blood vessel via the guiding catheter 310 as illustrated in FIG. 25B, and the debris D inside the filter portion 241 is suctioned into the sheath 230. The filter portion 241 is then accommodated inside the sheath 230 as illustrated in FIG. 26A. The filter instrument 240 together with the sheath 230 may then be retracted and removed from the living body. The guiding catheter 310 and the introducer sheath are removed, thereby completing the procedure.

While performing the procedure, the accommodation bag 182 supplies the physiological salt solution to the treatment device 20 at all times. Therefore, blood is prevented from flowing into the outer sheath 80, the drive shaft 60, the linear motion shaft 70, and the inner tube 100. Coagulation of blood inside the treatment device 20 is thus prevented. Therefore, deterioration of the operability of the treatment device 20 caused by coagulation of blood can be prevented, and a coagulated substance can also be prevented from flowing into a blood vessel. Safety is thus improved. In addition, since blood can be prevented from flowing to the outside via the medical device 10 (i.e., blood will not flow out of the living body), safety can be improved.

As described above, the medical device 10 according to the present embodiment is provided with the stretchable interlock portion 140 interlocking (i.e., connecting) the proximal portion of the drive shaft 60 and the proximal portion of the linear motion shaft 70 with each other while maintaining liquid-tight properties. The struts 41 can thus expand to incise the stenosed site S in accordance with movement of the linear motion shaft 70 in the axial direction with respect to (i.e., relative to) the drive shaft 60. In addition, due to the tubular interlock portion 140, liquid-tight properties between the drive shaft 60 and the linear motion shaft 70 can be maintained. Moreover, when the linear motion shaft 70 and the drive shaft 60 (which relatively move) are interlocked with each other by the stretchable interlock portion 140, there is no need to employ a seal structure such as an O-ring and the like generating friction. It is thus possible to reduce loss of the drive force. In addition, leakage of liquid supplied from the liquid feeding unit 180 to the inside of the drive shaft 60 can be prevented by the interlock portion 140 to allow the fluid to be effectively fed into the drive shaft 60 and the linear motion shaft 70. Blood can thus be effectively prevented from flowing into the medical device 10.

The linear motion shaft 70 receives rotary force not only from the distal side interlocked with the struts 41 but also from the proximal side by the interlock portion 140. Therefore, the linear motion shaft 70 is likely to rotate while following the drive shaft 60 without delay (i.e., synchronously or to rotate together with the driving shaft 60). Torsion on the linear motion shaft 70 due to rotational misalignment is thus prevented. When torsion of the linear motion shaft 70 can be prevented, the work for distorting the linear motion shaft 70 is no longer necessary, and the drive force can be effectively transmitted. Thus, it is possible to drive the linear motion shaft 70 at low torque.

The interlock portion 140 is positioned outside the human body during the procedure because the interlock portion 140 is proximal to the driven gear 64 of the drive shaft 60 (i.e., the gear portion of the drive shaft 60 that receives the rotary drive force). Therefore, safety can be ensured even if the interlock portion 140 breaks.

In addition, the interlock portion 140 may be configured to include a plurality of layers (members). Accordingly, the design freedom of the interlock portion 140 is increased. Therefore, it is possible to obtain high torque transmission performance while maintaining liquid-tight properties and stretching properties.

In addition, since the interlock portion 140 tolerates torsion of the proximal portion of the drive shaft 60 and the proximal portion of the linear motion shaft 70 in the rotation direction, the interlock portion 140 can absorb the misalignment in the rotation direction occurring between the linear motion shaft 70 and the drive shaft 60, by being distorted. The interlock portion 140 can thus promote smooth and natural rotations.

Since the interlock portion 140 is a pipe body (i.e., is tubular) which tapers in the direction toward the proximal side (i.e., tapers from its distal end towards its proximal end), the interlock portion 140 can maintain liquid-tight properties between the drive shaft 60 and the linear motion shaft 70 (i.e., no fluid flow beyond the proximal end of the interlock portion 140). A drive shaft 60 and linear motion shaft 70 having different outer diameters can be smoothly and naturally interlocked with each other by this tapered interlock portion 140.

The medical device 10 includes the inner tube 100 which is a pipe body (i.e., tubular) inside the tubularly-formed linear motion shaft 70. The inner tube 100 permits (i.e., does not restrain) rotation of the drive shaft 60 and the linear motion shaft 70. Therefore, even though the drive shaft 60 and the linear motion shaft 70 rotate, the inner tube 100 does not rotate. No rotary force acts on the wire and the like inserted into the inner tube 100. Therefore, in the medical device 10, abrasion of the wire and the like inserted into the inner tube 100 can be prevented, and the wire and the like can be prevented from rotating and from being pulled out (i.e., unintentionally removed from the inner tube 100). Since the inner tube 100 does not rotate, blood is unlikely to be drawn into the lumen 101 of the inner tube 100. Therefore, coagulation of blood inside the lumen 101 is inhibited from occurring. Deterioration of the operability of the medical device 10 can thus be prevented. Wire and the like within the inner tube 100 can be prevented from receiving friction force from the inner tube 100 and can be prevented from moving in the axial direction, and thus, a blood vessel can be prevented from being damaged (i.e., unintended damage to the blood vessel can be further avoided).

In the medical device 10 according to the present embodiment, the hole portions 61 and 71 penetrating the drive shaft 60 from the inner surface to the outer surface are formed in at least the drive shaft 60 from among the drive shaft 60 and the linear motion shaft 70 (i.e., the hole portions 61 are formed in the drive shaft and the hole portions 71 may be formed in the linear motion shaft 70). Therefore, when liquid such as a physiological salt solution and the like is supplied from the liquid feeding unit 180, the liquid can be supplied to at least the inside of the drive shaft 60 from among the inside of the drive shaft 60 and the inside of the linear motion shaft 70 via the hole portions 61 and 71. Blood is thus unlikely to flow into at least the drive shaft 60 from among the drive shaft 60 and the linear motion shaft 70. Therefore, coagulation of blood inside the medical device 10 is prevented, and relative movement between the pipe bodies (e.g., the shafts 60, 70) is appropriately maintained. Thus, deterioration of the operability can be prevented. When the liquid is supplied to at least the inside of the drive shaft 60 from among the inside of the drive shaft 60 and the inside of the linear motion shaft 70, blood can be prevented from flowing out from the human body via the medical device 10. Thus, safety can be improved.

The liquid supplied from the liquid feeding unit 180 to the inside of the outer sheath 80 can be prevented from leaking proximally by the first seal portion 185, which maintains liquid-tight properties of the proximal portion of the outer sheath 80 and the proximal portion of the drive shaft 60. Therefore, the fluid can be effectively fed into the drive shaft 60 and the linear motion shaft 70, and blood can be effectively prevented from flowing into the medical device 10.

Rotation of the inner tube 100 is not restrained with respect to the drive shaft 60 and the linear motion shaft 70. The hole portions 102 penetrating the inner tube 100 from the inner surface to the outer surface are formed so that the fluid can also be supplied from the liquid feeding unit 180 to the inside of the inner tube 100. Blood can thus be effectively prevented from flowing into the inner tube 100.

The treatment method disclosed here (a therapeutic method) involves incising a substance inside a biological lumen. The treatment method is performed by using a medical device which includes: a tubular drive shaft that is rotatable; a tubular outer sheath that can accommodate the drive shaft; at least one strut that is interlocked with a distal side of the drive shaft in a rotatable manner, extends along a rotary axis, and is expandable radially outward in response to flexure of an intermediate portion; a tubular linear motion shaft that is disposed inside the drive shaft, is relatively movable with respect to the drive shaft in an axial direction in order to cause the strut to expand, and is rotatable together with the drive shaft, and a liquid feeding unit that supplies liquid to a space between the outer sheath and the drive shaft. A hole portion penetrating the drive shaft from an inner surface to an outer surface is formed in at least the drive shaft from among the drive shaft and the linear motion shaft. The treatment method includes (i) a step of supplying liquid by the liquid feeding unit and supplying liquid to at least the inside of the drive shaft from among the inside of the drive shaft and the inside of the linear motion shaft via the hole portion formed in at least the drive shaft from among the drive shaft and the linear motion shaft, (ii) a step of inserting the strut into a biological lumen in a contraction state, (iii) a step of causing the strut to expand, (iv) a step of rotating the strut by the drive shaft and incising a substance inside the biological lumen, and (v) a step of causing the strut to contract and removing the strut from the inside of the biological lumen. In the treatment method having the above-described configuration, liquid is supplied to at least the inside of the drive shaft from among the inside of the drive shaft and the inside of the linear motion shaft. Therefore, blood is unlikely to flow into at least the drive shaft from among the drive shaft and the linear motion shaft. Coagulation of blood inside the treatment device is thus prevented, and relative movement between the pipe bodies is appropriately maintained (e.g., the shafts can move relative to one another). Thus, deterioration of the operability can be prevented. Blood can be prevented from flowing out via the medical device to improve safety.

The medical device includes the inner tube which is a pipe body disposed inside the drive shaft, of which rotation is not restrained with respect to the drive shaft and the linear motion shaft, and in which the hole portion penetrating the inner tube from the inner surface to the outer surface is formed. According to the above-described treatment method, liquid may be supplied by the liquid feeding unit so that the fluid is supplied to the inside of the drive shaft, the inside of the linear motion shaft, and the inside of the inner tube via the hole portions formed in the drive shaft, the linear motion shaft, and the inner tube. Accordingly, blood flow into the outer sheath, the drive shaft, the linear motion shaft, and the inner tube is regulated (i.e., prevented). Therefore, coagulation of blood inside the pipe bodies can be prevented, and relative movement between the pipe bodies (i.e., the shafts are movable relative to one another) can be appropriately maintained. Thus, deterioration of the operability can be prevented.

The disclosed medical device and method are not limited to only the above-described embodiment. Various changes can be made by those skilled in the art without departing from the technical scope of the present invention. For example, in the embodiment, the blades 47 are formed on only the distal side of the struts 41. However, the blades 47 may be formed on the proximal side of the struts or may be formed on both the distal side and the proximal side.

In addition, the form of the blade of the strut is not particularly limited as long as the blade can perform incision. For example, the edge portion of the strut on the outer side may be configured to be a blade.

In addition, the biological lumen is not limited to a blood vessel in which the medical device 10 is inserted. For example, the biological lumen may be a vessel, the urinary duct, the bile duct, the ovarian duct, the hepatic duct, and the like.

In addition, at least any one of the incision section 40 and the support section 50 may be coated with a coating layer made from a hydrophilic material. In this manner, at least any one of the incision section 40 and the support section 50 is likely to be slidable with respect to biological tissue. Therefore, normal biological tissue can be prevented from being damaged, and thus, safety can be enhanced (i.e., no unintended damage will be imparted on the body tissue).

In addition, in the above-described embodiment, the support section 50 is disposed radially inward in the struts 41. However, a portion of the wire material configured to be the support section may be disposed on the outer side of the strut. According to such a configuration, a portion of the strut which is not intended to be in contact with biological tissue is covered with the wire material, and thus, damage to normal biological tissue can be reduced.

In addition, in the above-described embodiment, the incision section 40 and the support section 50 can be caused to expand to have an arbitrary size (i.e., a size/outer diameter selected by the operator) by operating the operation unit 110. However, the incision section 40 and the support section 50 do not have to be expandable to have an arbitrary size. In addition, the incision section 40 and the support section 50 may have structures which expand due to the self-restoring force (i.e., are self-expanding).

In the above-described embodiment, the support section 50 is formed by braiding a plurality of wire materials 51. However, the support section 50 may be formed by reticularly forming a plurality of opening portions in one member.

In the above-described embodiment, in order to move the linear motion shaft 70, a feed screw mechanism is adopted. However, as long as the linear motion shaft 70 can be moved, the structure is not limited to a feed screw 191 or feed screw mechanism.

The above-described embodiment uses the motor to rotate the drive shaft 60. However, the drive source is not limited a motor. For example, the drive source may be a gas turbine which rotates by high-pressure gas such as nitrogen gas and the like.

Figure 27:
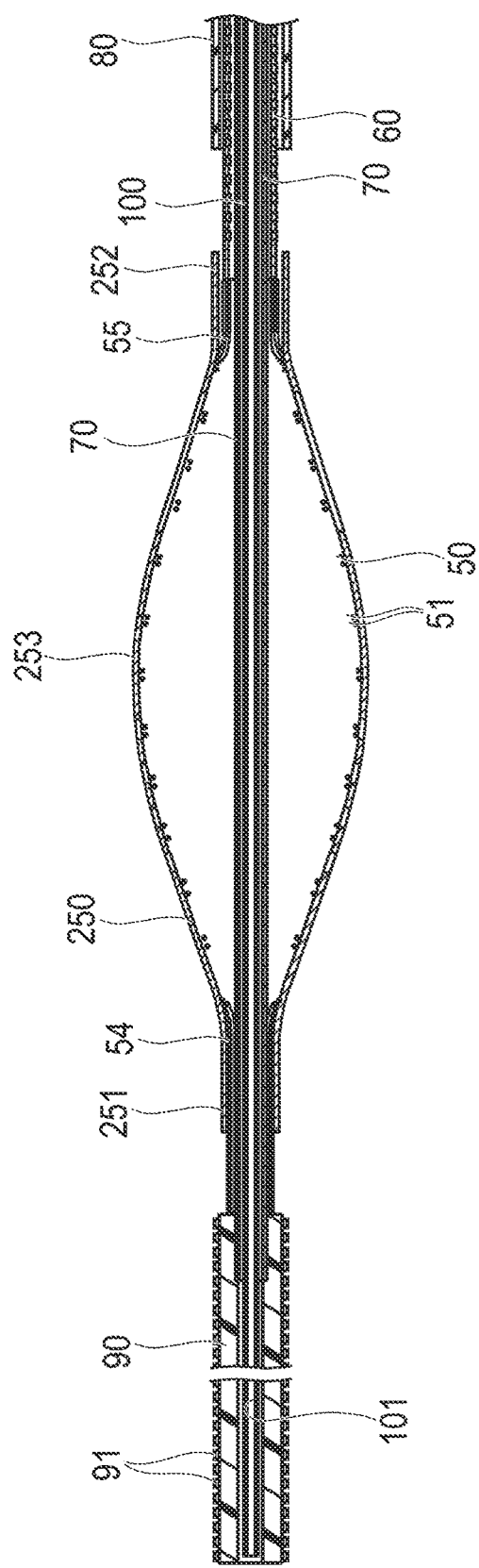
FIG. 27 is a longitudinal sectional view illustrating a modification example of the medical device of the embodiment.

In a modification example of the embodiment illustrated in FIG. 27, a distal end portion 251 of an incision section 250 is fixed to the distal side end portion 54 of the support section 50, and a proximal end portion 252 of the incision section 250 is not fixed to the proximal side end portion 55 of the support section 50 and the drive shaft 60 (i.e., it is a free end). Therefore, the proximal end portion 252 of the incision section 250 is movable in the axial direction relative to the proximal side end portion 55 of the support section 50 and the drive shaft 60. Note that, the proximal side end portion 55 of the support section 50 is fixed to the drive shaft 60, and the distal side end portion 54 of the support section 50 is fixed to the linear motion shaft 70. Even in such a configuration, when the distal side end portion 54 of the support section 50 and the proximal side end portion 55 are caused to be close to each other (i.e., to be moved closer or to reduce the space between the portions 54, 55), a strut 253 of the incision section 250 can expand by only the radially outward force received from the support section 50 without causing force in the axial direction to act between the distal end portion 251 and the proximal end portion 252 of the incision section 250. Note that, the same reference numerals and signs are applied to the portions having a function similar to that in the above-described embodiment, and description thereof will be omitted.

Figure 28:
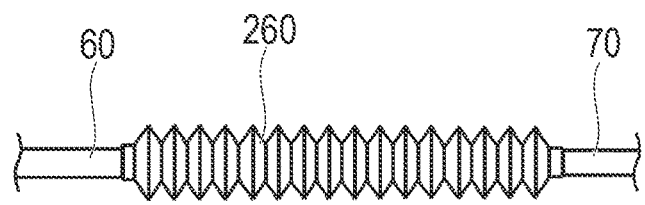
FIG. 28 is a plan view illustrating another modification example of the medical device of the embodiment.

In addition, as illustrated in another modification example of the embodiment in FIG. 28, a stretchable interlock portion 260 which interlocks the proximal portion of the linear motion shaft 70 and the proximal portion of the drive shaft 60 with each other may be formed to have a bellows shape. The interlock portion 260 is easily stretched in the axial direction due to the bellows shape. Note that, the same reference numerals and signs are applied to the portions having a function similar to that in the above-described embodiment, and description thereof will be omitted.

Figure 29:
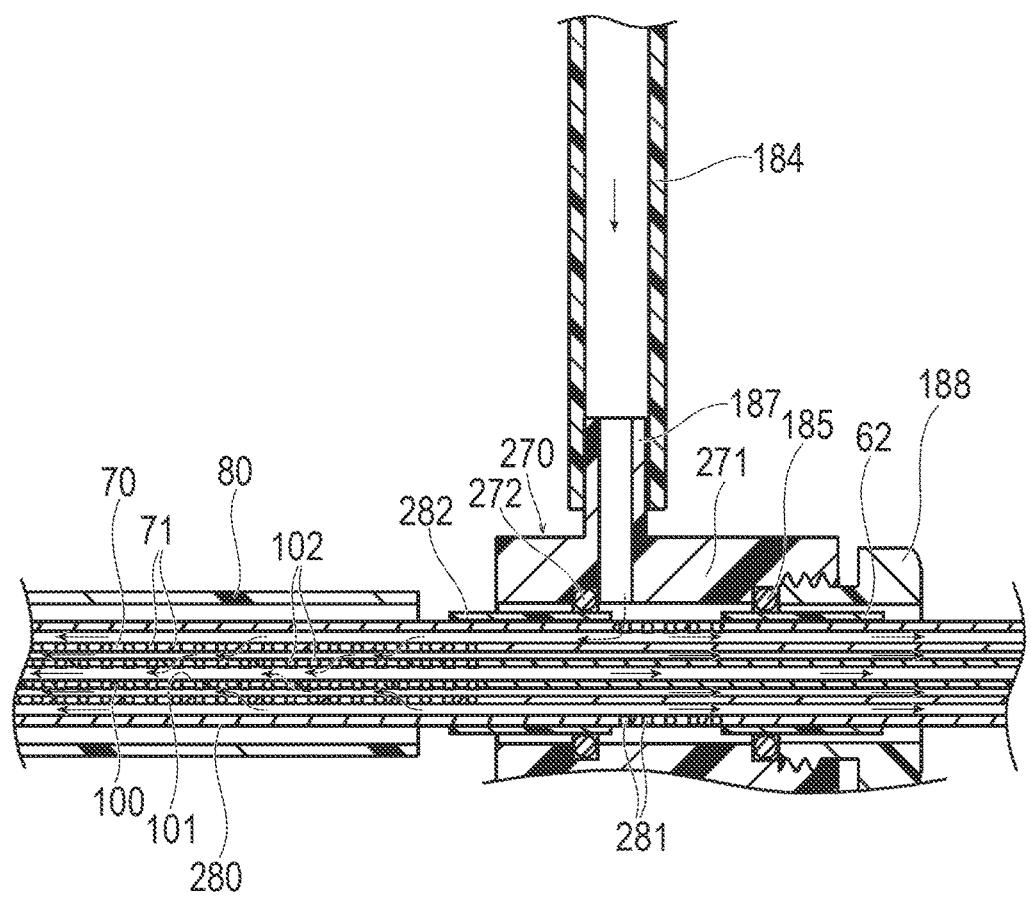
FIG. 29 is a sectional view illustrating another modification example of the medical device of the embodiment.

In addition, as illustrated in further another modification example of the embodiment in FIG. 29, the outer sheath 80 may not be interlocked with a first housing 271 of a liquid feeding unit 270, and a third seal portion 272 may be provided on a tip side from the port portion 187 provided in the first housing 271. In a drive shaft 280, hole portions 281 are formed between the first seal portion 185 and the third seal portion 272. The outer surface of the drive shaft 280 is coated with a second coating portion 282 which slidably comes into contact with the third seal portion 272 and reduces friction force. According to such a configuration, the physiological salt solution can flow into the space between the drive shaft 280 and the linear motion shaft 70 via the hole portions 281 without supplying a physiological salt solution from the accommodation bag 182 to the space between the outer sheath 80 and the drive shaft 280. The physiological salt solution flowing into the drive shaft 280 can pass through the hole portions 71 of the linear motion shaft 70 and can flow into the linear motion shaft 70. The physiological salt solution flowing into the linear motion shaft 70 can pass through the hole portions 102 of the inner tube 100 and can flow into the lumen 101 of the inner tube 100. Note that, the same reference numerals and signs are applied to the portions having a function similar to that in the above-described embodiment, and description thereof will be omitted.

Figure 30:
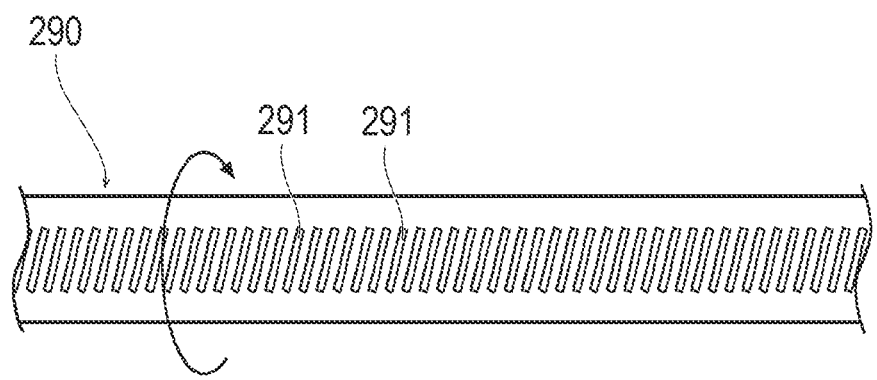
FIG. 30 is a plan view illustrating another modification example of the medical device of the embodiment.

As illustrated in another modification example of the embodiment in FIG. 30, hole portions 291 formed in a drive shaft 290 may be formed on the outer surface (and the inner surface) of the drive shaft 290 so as to incline with respect to the circumferential direction. Regarding the inclination of the hole portions 291, it is preferable that the hole portions 291 incline so as to tilt to the proximal side toward the rotation direction such that physical force acts to cause a physiological salt solution to flow in the direction toward the distal side in accordance with rotations of the drive shaft 290. According to such a configuration, an uneven spiral structure is formed due to a plurality of the inclined hole portions 291, and the uneven structure acts as a propeller in a pump, thereby applying a force to act on the physiological salt solution to move the physiological salt solution in the direction toward the distal side due to rotations of the drive shaft 290. Liquid-feeding (i.e., injection) can thus be physically induced due to the shapes of the hole portions 291. Therefore, leakage of a physiological salt solution on the proximal side can be prevented, and the physiological salt solution can flow against blood pressure. Note that, the drive shaft may be formed with a coil, a spring, a member in which spiral slits are formed in a pipe, or the like, so that gaps are configured to be the hole portions. These hole portions of the drive shaft may be formed to incline with respect to (i.e., in reference to) the circumferential direction. The winding direction of the coil, the spring, or the slits is determined to be a direction in which physical force acts so that the physiological salt solution flows in the direction toward the distal side. The hole portions formed in the linear motion shaft 70 and the inner tube 100 may also be formed on the outer surface (and the inner surface) so as to incline with respect to the circumferential direction.

Figure 31:
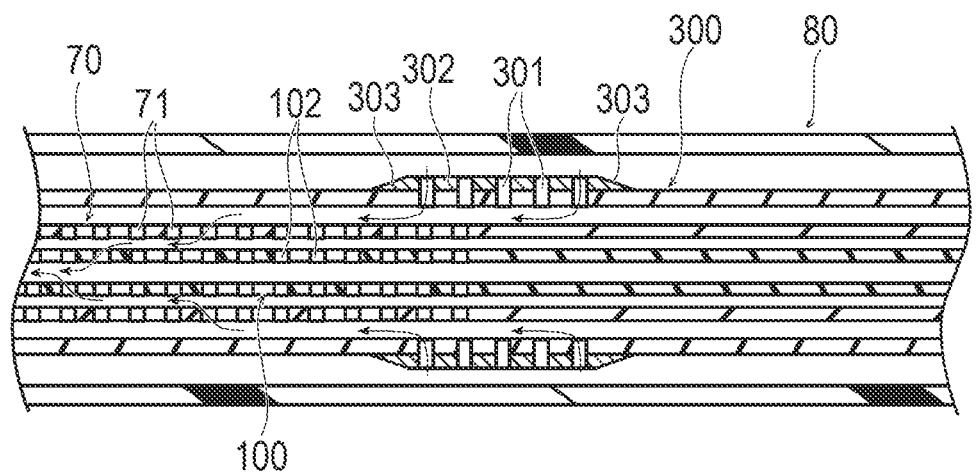
FIG. 31 is a sectional view illustrating another modification example of the medical device of the embodiment.

As illustrated in further another modification example of the embodiment in FIG. 31, a drive shaft 300 may have a reinforcement portion 302 which applies rigidity within a range in which hole portions 301 are formed (i.e., in the area/vicinity where the hole portions 301 penetrate the drive shaft 300). The reinforcement portion 302 has a configuration in which holes are formed in a tube (which is formed from metal or a resin) to penetrate the tube from the outer surface to the inner surface. In the end portion of the reinforcement portion 302, there is provided a taper portion 303 which is formed in a taper shape so that physical properties of the reinforcement portions 302 gradually change. The taper portion 303 reduces a radical change in the rigidity of the drive shaft 300 so that the drive shaft 300 is unlikely to be ruptured. In this manner, when the drive shaft 300 includes the reinforcement portion 302, deterioration of strength caused by forming the hole portions 301 is prevented. Therefore, the strength can be maintained, and a break and the like can be prevented. When the drive shaft 300 includes the reinforcement portion 302, it is possible to provide more hole portions 301 causing the deterioration of the strength, and thus, it is possible to enhance liquid-feeding properties. In order to reduce a radical change in the rigidity of the drive shaft in the end portion, the density of the reinforcement portion may vary so as to be lowered toward the end portion (i.e., to be less dense at the end portions). In addition, the configuration of the reinforcement portion is not particularly limited as long as the drive shaft can be reinforced. For example, a meshed member in which the wire material is braided and which is tubularly formed may be adopted. In addition, the reinforcement portion may be provided in a portion in which the hole portions of the linear motion shaft or the inner tube are formed. Note that, the same reference numerals and signs are applied to the portions having a function similar to that in the above-described embodiment, and description thereof will be omitted.

Figure 32:
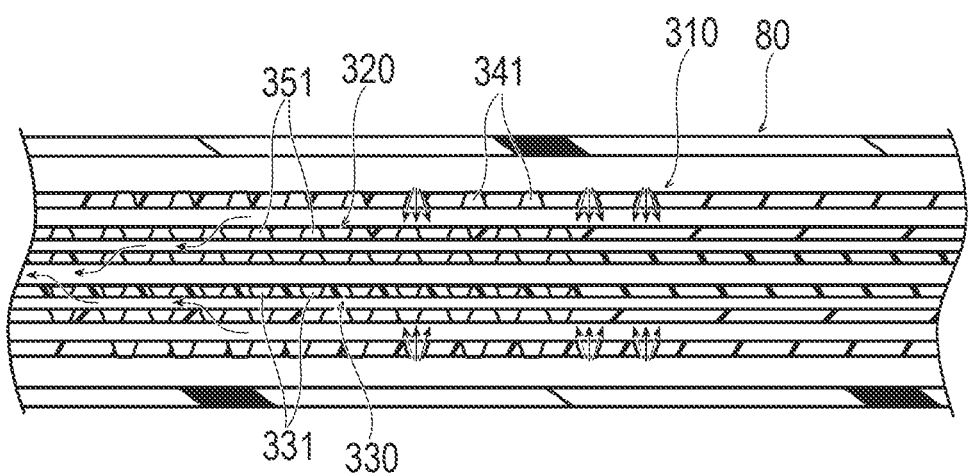
FIG. 32 is a sectional view illustrating another modification example of the medical device of the embodiment.

As illustrated in further another modification example of the embodiment in FIG. 32, hole portions 341 formed in a drive shaft 310, hole portions 351 formed in a linear motion shaft 320, and hole portions 331 formed in an inner tube 330 may be formed to have a funnel shape, for example, so that the cross section areas of the hole portions 331, 341, 351 are widened from the outer surface toward the inner surface. Accordingly, the physiological salt solution is likely to flow from the outer sheath 80 to the inside of the drive shaft 310, from the inside of the drive shaft 310 to the inside of the linear motion shaft 320, and from the inside of the linear motion shaft 320 to the inside of the inner tube 330. Liquid-feeding properties (i.e., fluid flow) can thus be enhanced. Note that, the same reference numerals and signs are applied to the portions having a function similar to that in the above-described embodiment, and description thereof will be omitted.

The detailed description above describes embodiments of a catheter and operational method representing examples of the inventive catheter and operation disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device for incising a substance inside a biological lumen, the medical device comprising:
    a tubular drive shaft that is rotatable about a rotary axis, the drive shaft possessing a distal portion, a proximal portion, and extending in an axial direction;
    an intermediate portion connected to the distal portion of the drive shaft, the intermediate portion being expandable radially outward;
    at least one strut interlocked with a distal portion of the drive shaft, the at least one strut being rotatable with the drive shaft, extending along the rotary axis and being expandable radially outward in response to radial outward expansion of the intermediate portion;
    a tubular linear motion shaft inside the drive shaft, the linear motion shaft being movable relative to the drive shaft in the axial direction to cause the strut to expand radially outward, the linear motion shaft being rotatable together with the drive shaft, the linear motion shaft possessing a proximal portion; and
    a tubular interlock portion that interlocks the proximal portion of the drive shaft and the proximal portion of the linear motion shaft while maintaining liquid-tight properties and is stretchable in the axial direction.

2. The medical device according to claim 1,
    wherein the drive shaft comprises a gear portion receiving a rotary drive force to rotate the drive shaft, and the interlock portion is proximal to the gear portion of the drive shaft receiving the rotary drive force.

3. The medical device according to claim 1, wherein the interlock portion includes a plurality of members.

4. The medical device according to claim 1,
    wherein the interlock portion is configured to absorb torsion due to misalignment occurring between the proximal portion of the drive shaft and the proximal portion of the linear motion shaft about the rotary axis.

5. The medical device according to claim 1,
    wherein the interlock portion is a tubular body possessing a distal end and a proximal end, and the interlock portion tapers in the axial direction from the distal end to the proximal end of the interlock portion.

6. The medical device according to claim 1, further comprising:
    an inner tube inside of the linear motion shaft, the inner tube being configured not to restrain rotation of the drive shaft and the linear motion shaft.

* * * * *